(12) United States Patent
Schreiber et al.

(10) Patent No.: US 7,811,594 B2
(45) Date of Patent: Oct. 12, 2010

(54) CROSSLINKED OIL DROPLET-BASED COSMETIC OR PHARMACEUTICAL EMULSIONS

(75) Inventors: Jörg Schreiber, Hamburg (DE); Khiet Hien Diec, Hamburg (DE)

(73) Assignee: Beiersdorf AG, Hamburg (DE)

( * ) Notice: Subject to any disclaimer, the term of this patent is extended or adjusted under 35 U.S.C. 154(b) by 1532 days.

(21) Appl. No.: 10/953,587

(22) Filed: Sep. 28, 2004

(65) Prior Publication Data

US 2005/0106199 A1    May 19, 2005

Related U.S. Application Data

(63) Continuation of application No. PCT/EP03/03167, filed on Mar. 27, 2003.

(30) Foreign Application Priority Data

Mar. 28, 2002  (DE) ................ 102 13 956

(51) Int. Cl.
*A61K 8/02* (2006.01)
(52) U.S. Cl. ..................... 424/401
(58) Field of Classification Search ............. 424/401
See application file for complete search history.

(56) References Cited

U.S. PATENT DOCUMENTS

| 4,567,161 A | 1/1986 | Posanski et al. |
| 5,360,458 A * | 11/1994 | Forsberg et al. ............ 44/301 |
| 5,401,634 A * | 3/1995 | Milbrath .................. 435/6 |
| 5,883,181 A * | 3/1999 | Cicchiello et al. .......... 524/521 |
| 5,929,030 A | 7/1999 | Hamied et al. |
| 6,245,349 B1 | 6/2001 | Yiv et al. |
| 6,468,551 B1 | 10/2002 | Diec et al. |
| 6,607,733 B1 | 8/2003 | Diec et al. |
| 6,613,338 B1 * | 9/2003 | Schreiber et al. ............ 424/401 |
| 2001/0007663 A1 | 7/2001 | Von Corswant |
| 2002/0146375 A1 | 10/2002 | Schreiber et al. |
| 2003/0083314 A1 | 5/2003 | Yiv et al. |

FOREIGN PATENT DOCUMENTS

| EP | 885 914 B1 | 6/1998 |
| WO | WO 95 26707 | 10/1995 |
| WO | WO 96/28132 | 9/1996 |
| WO | WO 98/15255 | 4/1998 |
| WO | WO 00/37042 | 6/2000 |

(Continued)

OTHER PUBLICATIONS

"Effect of phospholipid emulsifiers on physicochemical properties of intravenous fat emulsions and/or drug carrier emulsions" 1990 J. Pharm. Pharmacol., 42: p. 513-515.

(Continued)

*Primary Examiner*—Robert A Wax
*Assistant Examiner*—Aradhana Sasan
(74) *Attorney, Agent, or Firm*—Greenblum & Bernstein, P.L.C.

(57) ABSTRACT

The invention is a crosslinked water-in-oil emulsion that is useful in cosmetic and pharmaceutical applications. The emulsion includes a water phase, oil phase, water-in-oil emulsifier, and one or more crosslinkers. The crosslinkers that are useful in the invention include molecules having at least one hydrophilic region and at least one hydrophobic region. The invention also includes a process for preparing the crosslinked emulsion.

29 Claims, 2 Drawing Sheets

FOREIGN PATENT DOCUMENTS

| | | |
|---|---|---|
| WO | WO 00/56366 | 9/2000 |
| WO | WO 00/61098 | 10/2000 |

OTHER PUBLICATIONS

International Search Report dated Oct. 16, 2003 from International Application No. PCT/EP03/03166.

International Search Report dated Oct. 16, 2003 from International Application No. PCT/EP03/03167.

International Search Report dated Oct. 6, 2003 from International Application No. PCT/EP03/02983.

German Search Report dated Dec. 13, 2002 from German Application No. 102 13 957.1.

German Search Report dated Dec. 13, 2002 from German Application No. 102 103 956.3.

German Search Report dated Dec. 13, 2002 from German Application No. 102 13 955.5.

* cited by examiner

CROSSLINKED OIL DROPLET-BASED COSMETIC OR PHARMACEUTICAL EMULSIONS

CROSS-REFERENCE TO RELATED APPLICATIONS

This is a continuation application of PCT/EP03/03167, filed Mar. 27, 2003, which is incorporated herein by reference in its entirety, and also claims the benefit of German Priority Application No. 102 13 956.3, filed Mar. 28, 2002.

FIELD OF THE INVENTION

The present invention relates to emulsions of the oil-in-water type, to processes for their preparation, and to their use for cosmetic or pharmaceutical purposes. In particular, they are applied topically, used as impregnation medium for wipes or foamed.

BACKGROUND OF THE INVENTION

Cosmetic skincare is primarily understood as meaning that the natural function of the skin as a barrier against environmental influences (e.g. dirt, chemicals, and microorganisms) and against the loss of substances intrinsic to the body (e.g. water, natural fats, electrolytes) is strengthened or restored.

Impairment of this function may lead to increased absorption of toxic or allergenic substances or to attack by microorganisms, leading to toxic or allergic skin reactions.

Another aim of skincare is to compensate for the loss by the skin of lipids and water caused by daily washing. This is particularly important when the natural regeneration ability is inadequate. Furthermore, skincare products should protect against environmental influences, in particular against sun and wind, and delay skin aging.

Medicinal topical compositions generally comprise one or more medicaments in an effective concentration. For the sake of simplicity, for a clear distinction between cosmetic and medicinal use and corresponding products, reference is made to the legal provisions of the Federal Republic of Germany (e.g. Cosmetics Directive, Foods and Drugs Act).

Customary cosmetic and dermatological preparation forms which have become ever more widespread in recent times are gels.

In simple emulsions, finely disperse droplets of one phase (water droplets in water-in-oil (W/O) emulsions or lipid vesicles in oil-in-water (O/W) emulsions), surrounded by an emulsifier shell, are present in a second phase. The droplet diameters of customary emulsions are in the range from about 200 μm to about 50 μm. Such "macroemulsions" are, without further coloring additives, milky white in color and opaque.

The use of customary cosmetic emulsifiers is in itself safe. Nevertheless, emulsifiers, like ultimately any chemical substance, may in individual cases cause allergic reactions or reactions based on user hypersensitivity.

For example, it is known that certain photodermatoses are triggered by certain emulsifiers, but also by various fats, and simultaneous exposure to sunlight. Such photodermatoses are also called "Mallorca acne". One object of the present invention was therefore to develop sunscreen products.

SUMMARY OF THE INVENTION

Thus, the present invention relates, as particular embodiments, to cosmetic and dermatological photoprotective preparations, in particular skincare cosmetic and dermatological photoprotective preparations.

The harmful effect of the ultraviolet part of solar radiation on the skin is generally known. While rays with a wavelength of less than 290 nm (the so-called UVC region) are absorbed by the ozone layer in the earth's atmosphere, rays in the range between 290 nm and 320 nm, the so-called UVB region, cause erythema, simple sunburn or even burns of greater or lesser severity. The erythema activity maximum of sunlight is generally stated as the relatively narrow range around 308 nm.

Numerous compounds are known for protecting against UVB radiation; these are mostly derivatives of 3-benzylidenecamphor, of 4-aminobenzoic acid, of cinnamic acid, of salicylic acid, of benzophenone and also of 2-phenylbenzimidazole.

For the range between 320 nm and about 400 nm, the so-called UVA region, it is also important to have available filter substances since rays of that region can also cause damage. For example, it has been proven that UVA radiation leads to damage of the elastic and collagenous fibers of connective tissue, causing premature aging of the skin, and that it is to be regarded as a cause of numerous phototoxic and photoallergic reactions. The harmful effect of UVB radiation can be intensified by UVA radiation. UV radiation can, however, also lead to photochemical reactions, in which case the photochemical reaction products then intervene in the skin's metabolism.

In order to prevent these reactions, antioxidants or free-radical scavengers can additionally be incorporated into the cosmetic and dermatological formulations.

Most of the inorganic pigments which are known for use in cosmetics for protecting the skin against UV rays are UV absorbers or UV reflectors. These pigments are oxides of titanium, zinc, iron, zirconium, silicon, manganese, aluminum, cerium and mixtures thereof, and also modifications.

Crosslinked creams are also suitable for other cosmetic dermatological applications, for example deodorants, meaning that the present invention relates, in a particular embodiment, to these creams as a basis for cosmetic deodorants.

Cosmetic deodorants serve to eliminate body odor which arises when fresh perspiration, which is in itself odorless, is decomposed by microorganisms. Customary cosmetic deodorants are based on different active principles. In so-called antiperspirants, the formation of perspiration can be reduced by astringents, chiefly aluminum salts such as aluminum hydroxychloride (aluminum chlorohydrate). By using antimicrobial substances in cosmetic deodorants it is possible to reduce the bacterial flora on the skin. In an ideal case, only the odor-causing microorganisms would be effectively reduced. The flow of perspiration itself is not influenced by this, and in an ideal case only microbial decomposition of the perspiration is temporarily stopped. The combination of astringents with antimicrobial substances in one and the same composition is also customary.

Deodorants should satisfy the following conditions:

1) They should effect reliable deodorization.
2) The natural biological processes of the skin must not be impaired by the deodorants.
3) The deodorants must be harmless in the event of an overdose or other use which is not in accordance with the directions.
4) They should not become concentrated on the skin following repeated application.
5) They should be easy to incorporate into customary cosmetic formulations.

Liquid deodorants, for example aerosol sprays, roll-ons and the like, and also solid preparations, for example deodorant sticks, powders, powder sprays, intimate cleansing compositions etc. are known and customary.

The use of creams as bases for deodorizing or antiperspirant preparations are also known. Their relatively high content of emulsifiers, together with the described disadvantages, has hitherto been a shortcoming which is in need of remedying.

A further object of the present invention was therefore to develop preparations which are suitable as bases for cosmetic deodorants or antiperspirants and do not have the disadvantages of the prior art.

It was also an object of the invention to develop cosmetic bases for cosmetic deodorants which are characterized by good skin compatibility.

In addition, it was an object of the present invention to make available products based on crosslinked emulsions having the broadest possible application diversity. For example, bases for preparation forms such as cleansing products, face care and body care preparations were to be provided, but also decidedly medicinal-pharmaceutical administration forms, for example preparations against acne and other skin phenomena.

In a particular embodiment, the invention therefore relates to face cleansing products, preferably make-up removers, for example eye make-up removers or face care and body care creams/lotions, make-up removal emulsions, cleansing creams/lotions, sunscreen creams/lotions, antiwrinkle creams, hair creams, repellant creams, aftersun emulsions, shower creams, aftershave emulsions, shaving creams, deodorant/antiperspirant emulsions, antiacne creams/lotions.

Water-resistant eye make-up, for example mascara, can only be removed satisfactorily with aqueous-based make-up removers containing specific surfactants. However, these surfactants often only have limited physiological compatibility. When such substances come into contact with the mucous membrane, in particular the mucous membrane of the eye, they lead to irritations which manifest themselves, for example, in a reddening of the eyes. Reactions of this type are typical of surfactant-containing products. An object of the present invention was therefore to remedy such problems.

In a further embodiment, the present invention relates to hair cosmetic preparations. In particular, the present invention relates to hair cosmetic preparations for the care of hair and the scalp. In a preferred embodiment, the present invention relates to preparations which serve to strengthen individual hairs and impart hold and body to the hairstyle overall.

Roughly speaking, human hair can be divided into the living part, the hair root, and the dead part, the hair shaft. The hair shaft in turn comprises the medulla which, however, as result of evolution, has become insignificant for modern man and has receded, and in cases of thin hair is often entirely absent, and also the cortex surrounding the medulla and the cuticula which encloses the totality of medulla and cortex.

The cuticula in particular, but also the keratinous region between the cuticula and cortex, as the outer sheath of the hair, are exposed to particular demands as a result of environmental influences, as a result of combing and brushing, but also as a result of hair treatment, in particular hair coloring and hair shaping, e.g. permanent waving processes.

If the stress is particularly aggressive, for example bleaching with oxidizing agents such as hydrogen peroxide, in which the pigments distributed within the cortex are destroyed by oxidation, the inside of the hair can also be affected. If human hair is to be colored permanently, in practice only oxidizing hair coloring processes are suitable. During the oxidative coloring of hair, the dye chromophores are formed as a result of the reaction of precursors (phenols, aminophenols, and less frequently also diamines) and bases (in most cases p-phenylenediamine) with the oxidizing agent, in most cases hydrogen peroxide. Hydrogen peroxide concentrations of about 6% are usually used for this.

It is usually assumed that besides the coloring action, a bleaching action also takes place as a result of the hydrogen peroxide. In oxidatively colored human hair, as in the case of bleached hair, microscopic holes are detectable at the points where melanin granules were present. The fact is that the oxidizing agent hydrogen peroxide can react not only with the dye precursors, but also with the hair substance and as a result can cause damage to the hair under certain circumstances.

Washing the hair with aggressive surfactants can also stress the hair, and at least reduce its appearance or the appearance of the hairstyle overall. For example, certain water-soluble constituents of the hair (e.g. urea, uric acid, xanthine, keratin, glycogen, citric acid, lactic acid) can be leached out as result of hair washing.

For these reasons, some hair care cosmetics which are intended to be rinsed out of the hair again once they have acted, and some of those which are to remain on the hair have been used for a relatively long time. The latter can be formulated such that they not only serve to care for the individual hairs, but also improve the appearance of the hairstyle overall, for example by imparting more body to the hair, fixing the hairstyle over a longer period or improving its ease of styling.

By using quaternary ammonium compounds, for example, the combability of the hair can be decisively improved. Such compounds attach to the hair and are often still detectable on the hair after the hair has been washed a number of times.

However, the prior art has lacked active ingredients and preparations which satisfactorily care for damaged hair. Preparations which were intended to give body to the hairstyle have also often proven to be inadequate, or they were at least unsuitable for use as hair care preparations. The hairstyle-fixing preparations of the prior art generally comprise, for example, viscous constituents, which run the risk of giving rise to a feeling of stickiness, which often has to be compensated for by skillful formulation. An object was therefore also to overcome these the disadvantages of the prior art.

A particular object of the present invention was to make available preparations based on finely disperse, crosslinked emulsions of the oil-in-water type with the lowest possible emulsifier content which do not have the disadvantages of the prior art and which can be used for a very wide variety of cosmetic and dermatological applications, for example the uses described above. A further object of the invention was to enrich the limited range of preparations based on finely disperse, crosslinked emulsions of the oil-in-water type of the prior art.

Processes for the preparation of O/W microemulsion gels by crosslinking hydrophobically modified water-soluble polymers have been described in WO 9628132.

Lecithin-containing microemulsions for cosmetic, pharmaceutical, parenteral applications are known from the literature and patents (see WO 9815255). It is explained therein how lecithin-containing microemulsions based on ethylene oxide-free emulsifiers can be crosslinked to give the corresponding gels. WO 0037042 describes gels which, besides lecithin, comprise an O/W and a W/O emulsifier, and water. Crosslinking with hydrophobically modified water-soluble polymers to give lecithin-containing emulsions is not described.

A disadvantage of viscous O/W emulsions of the prior art is also that, without thickeners (low-viscosity O/W emulsions), they are advantageously finely divided (for example PIT emulsions) and often only convert to more coarsely particulate O/W droplets by adding the thickeners (polymers) as a result of interaction of the finely divided droplets with the thickener polymer backbone. Correspondingly dispersed active ingredients are therefore often less well distributed than before the addition of thickener since the droplets partially coalesce and form relatively large droplets or agglomerates. In addition, on the skin, this can lead to a hindered release of active ingredient or the emulsion forms disadvantageous lipid films following evaporation of the water, which leads to reduced absorption of the emulsion residue. The addition of a crosslinker (which does not influence/influences only slightly the droplet size) or the combination of a crosslinker with a noncrosslinking polymer (classic thickener, hydrocolloid) has not been described as being advantageous in this sense. These objects are achieved according to the invention.

BRIEF DESCRIPTION OF THE DRAWINGS

Having thus described the invention in general terms, reference will now be made to the accompanying drawings, wherein

Figure 1:
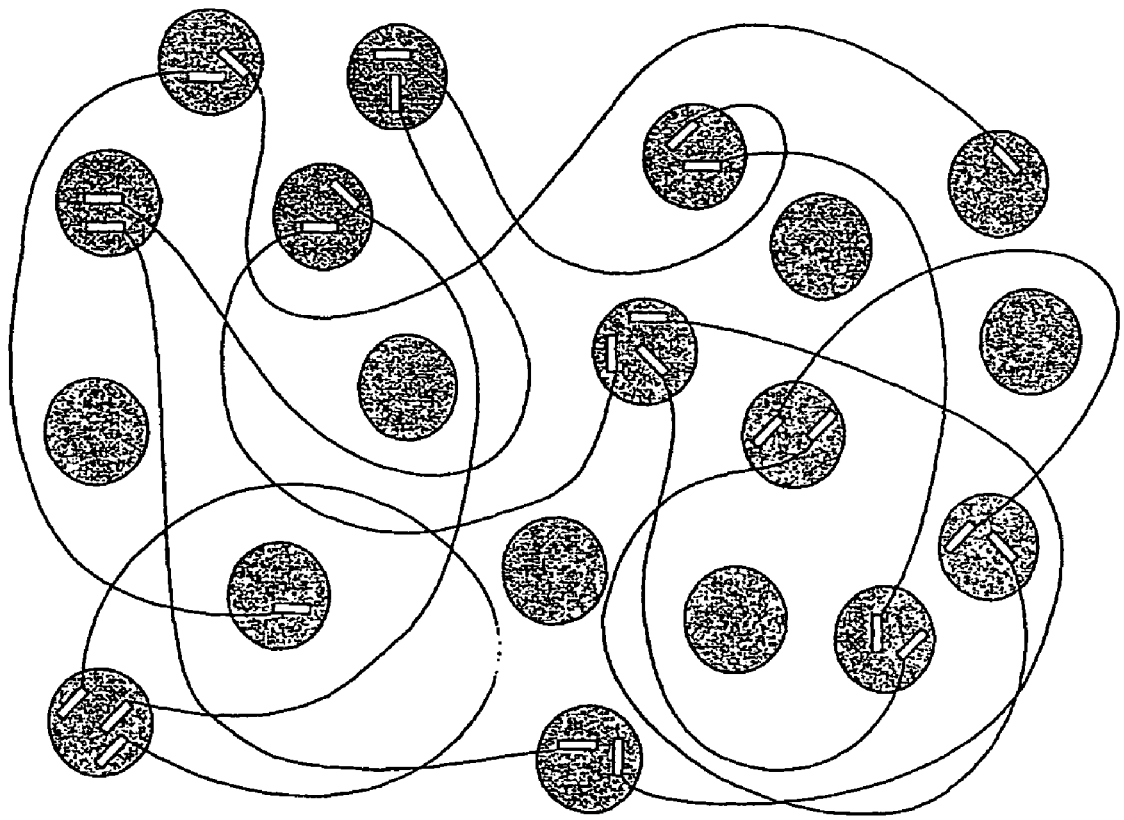
Figure 2:
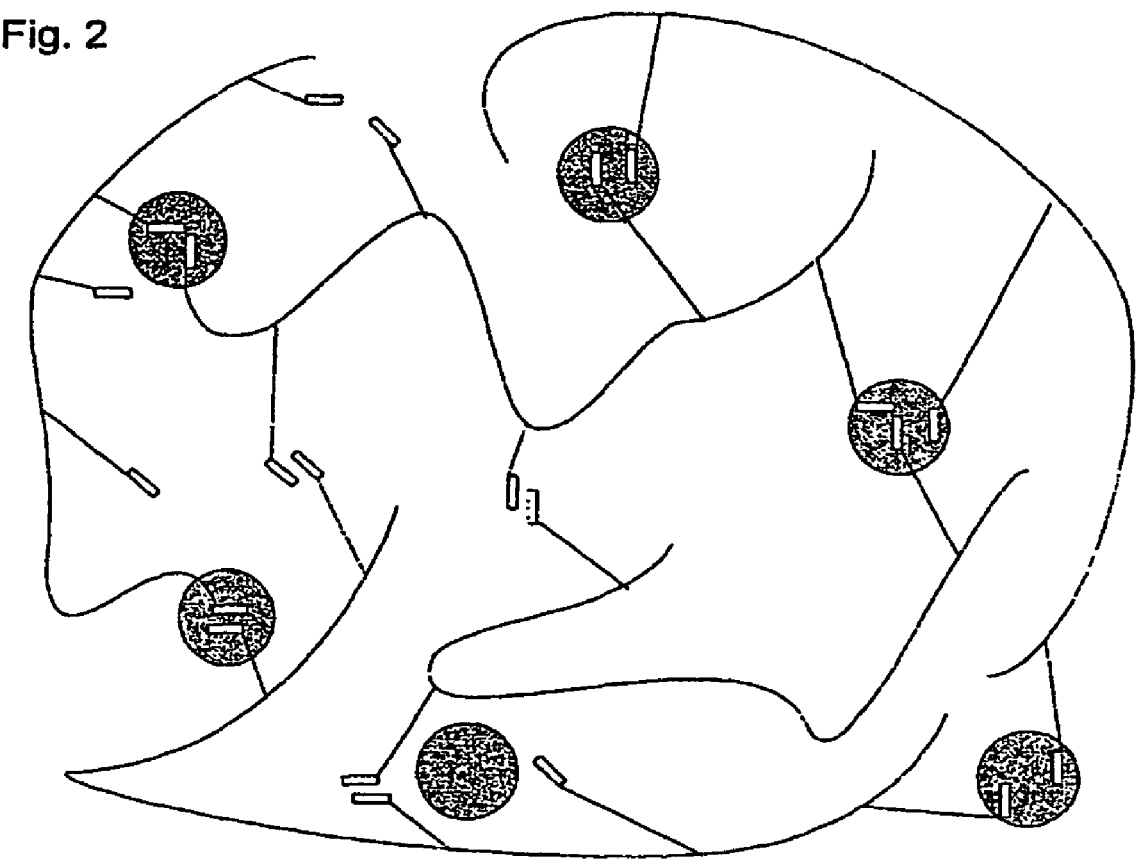

FIGS. 1 and 2 are drawings that illustrate the backbone of a water-soluble or water-dispersible crosslinker, where the branching points represent hydrophobic groups (symbolized by rectangles) bonded covalently to the polymer.

DETAILED DESCRIPTION OF THE INVENTION

The invention provides a process for preparing emulsions of the oil-in-water type, comprising a water phase and an oil phase, which is composed essentially of difficultly volatile constituents, comprising at least one oil-in-water emulsifier and optionally a water-in-oil emulsifier and at least one crosslinker, and if desired auxiliaries, additives and active ingredients, a) obtainable by adding the water phase with its constituents to the oil phase with its constituents, the O/W emulsifier and optionally the W/O emulsifier, and where one crosslinker or two or more crosslinkers are added to the water phase or the oil phase or to both phases, where an increase in viscosity arises and crosslinked O/W emulsions are-obtained, b) obtainable by bringing the mixture to a temperature within or outside of the phase-inversion temperature range and then cooling to room temperature, where an increase in viscosity arises and crosslinked O/W emulsions are obtained, or c) obtainable by adding the crosslinker subsequently to a low-viscosity O/W emulsion and obtaining crosslinked O/W emulsions.

The droplets of the discontinuous oil phase are joined together by one or more crosslinker substances. The crosslinker structure is characterized by at least one hydrophilic region which has an expansion which is suitable for bridging the distance between the emulsion droplets, and by at least one hydrophobic region, in particular at least two hydrophobic regions, which are able to hydrophobically interact with the emulsion droplets. If only one hydrophobic region is present, emulsions may arise in which entanglements of the hydrophilic domains of two or more polymers arise. In this way too, a crosslinked O/W emulsion is obtained.

Here, it is equally advantageous if the crosslinker substance forms an independent gel network in which the emulsion droplets are then held by hydrophobic interaction (so-called associative thickeners are then present), or whether the network is held together as a result of the crosslinking with the emulsion droplets at points of intersection in the network.

The droplet diameters of the preparations according to the invention are preferably in the ranges specified at the beginning.

Surprisingly, the droplet size distribution curve of the low-viscosity emulsion does not change, or changes only slightly, compared with the crosslinked emulsion, in contrast to the viscosity increase of low-viscosity emulsions containing classic thickeners in which an increase in the size of the original droplets is observed.

The invention therefore also provides the use of crosslinkers for stabilizing the droplet size of low-viscosity O/W emulsions during the increase in viscosity.

The crosslinker substances (one or more) used advantageously according to the invention generally follow structure schemes as follows:

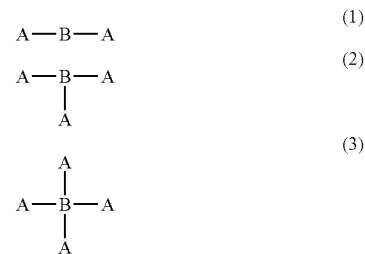

where B symbolizes a hydrophilic region of the particular crosslinker molecule, and A is in each case hydrophobic regions whose chemical nature may differ even within one molecule.

But also structure schemes such as

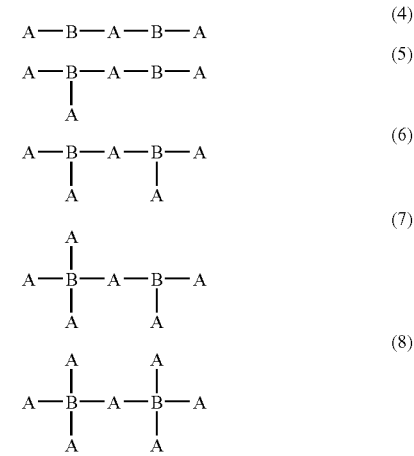

and analogously formed, yet more complex structures are definitely within the scope of the invention presented here.

The scope of the invention presented here likewise includes structure schemes as follows:

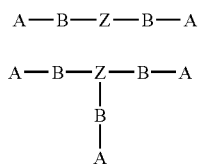
(9)

(10)

ylene chains of equal or unequal length, and whose terminal OH groups are esterified with a longer-chain fatty acid. Partial substitution on glycerol is also conceivable, as a result of which structures may form which correspond to scheme (9).

The hydrophilic groups B can advantageously be chosen such that the crosslinker overall is soluble in water or at least dispersible in water, in which case the hydrophobic moiety of groups A should then be overcompensated.

For structure scheme (1), the following more specific structure schemes may, for example, be obeyed:

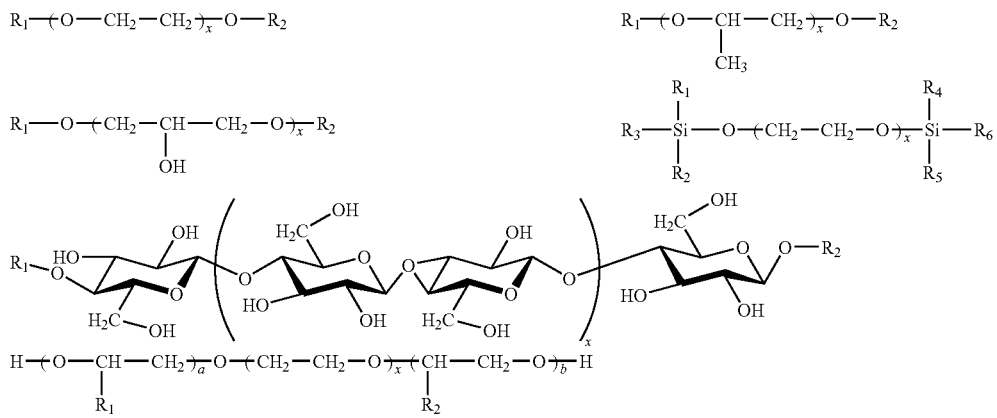

-continued

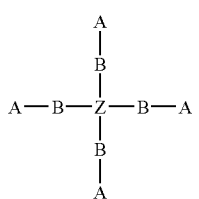
(11)

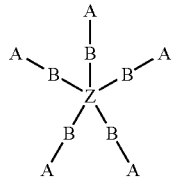
(12)

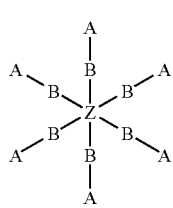
(13)

where $R_1$, $R_2$, $R_3$, $R_4$, $R_5$ and $R_6$, independently of one another, may be branched or unbranched, saturated or unsaturated, cyclic or chain-like aliphatic, aromatic or heteroaromatic radicals, for example branched or unbranched or cyclic alkyl or alkanoyl radicals, aryl or aroyl radicals which are unsubstituted or substituted by alkyl or aryl substituents, or else alkylated or arylated organylsilyl radicals. Here, x is numbers which allow the overall molecule to be soluble or at least dispersible in water, typically chosen from the range greater than 10, advantageously from the range 20 to 300, and a and b are numbers which are chosen depending on x such that the overall molecule has at least adequate solubility or dispersibility in water. In individual cases, for example when the crosslinker is chosen from the group of derivatized polysaccharides, x may also assume even essentially higher values than 300, even several million. This is known per se to the person skilled in the art and requires no further explanation.

For structure scheme (2), the following more specific structure schemes may, for example, be obeyed:

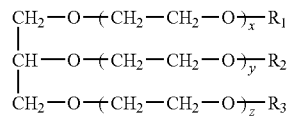

where Z is a central unit which may be hydrophilic or hydrophobic and generally consists of an oligofunctional or polyfunctional molecular radical. Crosslinkers with a higher degree of branching are of course also within the scope of the present invention.

For example, Z in scheme (10) can consist of a glyceryl radical whose three OH functions merge into the regions B, which for their part may, for example, represent polyoxyethwhere $R_1$, $R_2$ and $R_3$, independently of one another, may be branched or unbranched, saturated or unsaturated, cyclic or chain-like aliphatic, aromatic or heteroaromatic radicals, for example branched or unbranched or cyclic alkyl or alkanoyl radicals, aryl or aroyl radicals which are unsubstituted or substituted by alkyl or aryl substituents, or else alkylated or arylated organylsilyl radicals. x, y and z here, independently of one another, are numbers which allow the overall molecule to be soluble or at least dispersible in water, typically chosen from the range greater than 10, advantageously from the range 20 to 300.

Partial substitution is also conceivable here, where one or more of the indices x, y or z can assume the value zero and one or more of the radicals $R_1$, $R_2$, or $R_3$ can represent hydrogen atoms.

For structure scheme (3), the following more specific structure schemes may, for example, be obeyed:

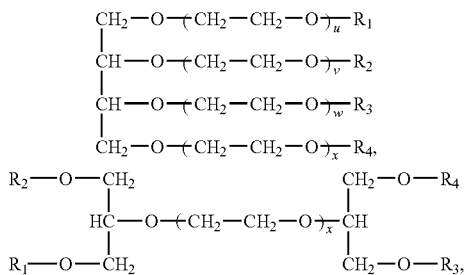

where $R_1$, $R_2$, $R_3$ and $R_4$, independently of one another, may be branched or unbranched, saturated or unsaturated, cyclic or chain-like aliphatic, aromatic or heteroaromatic radicals, for example branched or unbranched or cyclic alkyl or alkanoyl radicals, aryl or aroyl radicals which are unsubstituted or substituted by alkyl or aryl substituents, or else alkylated or arylated organylsilyl radicals. u, v, w and x here are, independently of one another, numbers which allow the overall molecule to be soluble or at least dispersible in water, typically chosen from the range greater than 10, advantageously from the range 20 to 300.

Here too it is of course possible for partial substitution to be conceivable, in which case one or more of the indices u, v, w, x can assume the value zero, and one or more of the radicals $R_1$, $R_2$, $R_3$, or $R_4$ can represent hydrogen atoms. The substances naturally convert to other structure schemes.

For structure scheme (9), the following more specific structure schemes, for example, may be obeyed:

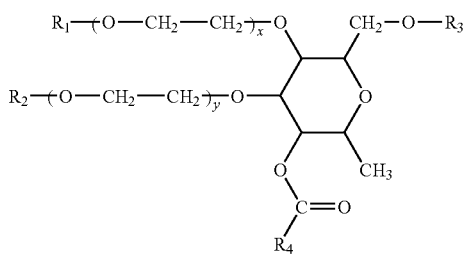

where $R_1$, $R_2$, $R_3$, and $R_4$, independently of one another, may be branched or unbranched, saturated or unsaturated, cyclic or chain-like aliphatic, aromatic or heteroaromatic radicals, for example branched or unbranched or cyclic alkyl or alkanoyl radicals, aryl or aroyl radicals which are unsubstituted or substituted by alkyl or aryl substituents, or else alkylated or arylated organylsilyl radicals. x and y here, independently of one another, are numbers which allow the overall molecule to be soluble or at least dispersible in water, typically chosen from the range greater than 10, advantageously from the range 20 to 300.

For structure scheme (10), the following more specific structure schemes, for example, may be obeyed:

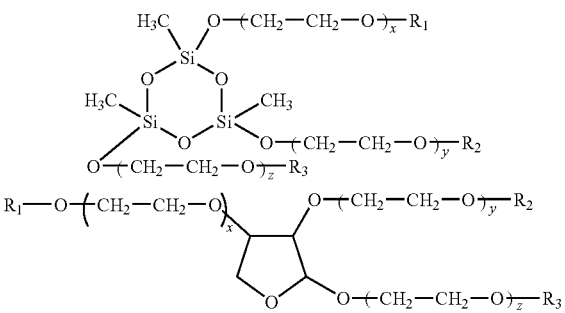

where $R_1$, $R_2$, and $R_3$, independently of one another, may be branched or unbranched, saturated or unsaturated, cyclic or chain-like aliphatic, aromatic or heteroaromatic radicals, for example branched or unbranched or cyclic alkyl or alkanoyl radicals, aryl or aroyl radicals which are unsubstituted or substituted by alkyl or aryl substituents, or else alkylated or arylated organylsilyl radicals. x, y and z here, independently of one another, are numbers which allow the overall molecule to be soluble or at least dispersible in water, typically chosen from the range greater than 10, advantageously from the range 20 to 300.

For structure scheme (11), the following more specific structure scheme, for example, may be obeyed:

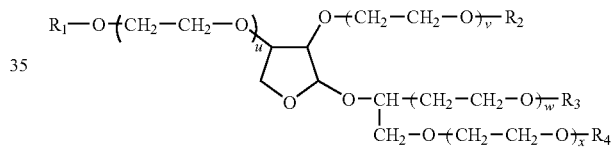

where $R_1$, $R_2$, $R_3$ and $R_4$, independently of one another, may be branched or unbranched, saturated or unsaturated, cyclic or chain-like aliphatic, aromatic or heteroaromatic radicals, for example branched or unbranched or cyclic alkyl or alkanoyl radicals, aryl or aroyl radicals which are unsubstituted or substituted by alkyl or aryl substituents, or else alkylated or arylated organylsilyl radicals. u, v, w and x here are, independently of one another, numbers which allow the overall molecule to be soluble or at least dispersible in water, typically chosen from the range greater than 10, advantageously from the range 20 to 300. k, l, m and n here, independently of one another, may be numbers from 0 to 50.

For structure scheme (12), the following more specific structure scheme, for example, may be obeyed:

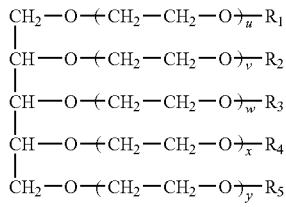

where $R_1$, $R_2$, $R_3$, $R_4$ and $R_5$, independently of one another, may be branched or unbranched, saturated or unsaturated, cyclic or chain-like aliphatic, aromatic or heteroaromatic radicals, for example branched or unbranched or cyclic alkyl or alkanoyl radicals, aryl or aroyl radicals which are unsubstituted or substituted by alkyl or aryl substituents, or else alkylated or arylated organylsilyl radicals. u, v, w, x and y here, independently of one another, are numbers which allow the overall molecule to be soluble or at least dispersible in water, typically chosen from the range greater than 10, advantageously from the range 20 to 100.

For structure scheme (13), the following more specific structure scheme, for example, may be obeyed:

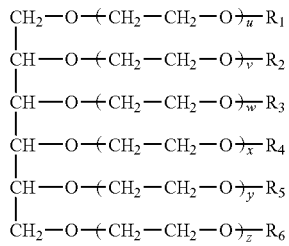

where $R_1$, $R_2$, $R_3$, $R_4$, $R_5$ and $R_6$, independently of one another, may be branched or unbranched, saturated or unsaturated, cyclic or chain-like aliphatic, aromatic or heteroaromatic radicals, for example branched or unbranched or cyclic alkyl or alkanoyl radicals, aryl or aroyl radicals which are unsubstituted or substituted by alkyl or aryl substituents, or else alkylated or arylated organylsilyl radicals. u, v, w, x, y and z here, independently of one another, are numbers which allow the overall molecule to be soluble or at least dispersible in water, typically chosen from the range greater than 10, advantageously from the range 20 to 1000.

In some cases, it is also advantageous to modify the structure schemes described above such that branching arises again at the end of the crosslinker molecule, for example in such a way as is realized in the group of so-called dendrimers.

Particularly suitable crosslinkers which have proven useful are those chosen from the group of:

polyethylene glycol ethers of the general formula R—O—(—$CH_2$—$CH_2$—O—)$_n$—R', where R and R', independently of one another, are branched or unbranched alkyl, aryl or alkenyl radicals and n is a number greater than 100;

etherified fatty acid ethoxylates of the general formula R—COO—(—$CH_2$—$CH_2$—O—)$_n$—R', where R and R', independently of one another, are branched or unbranched alkyl, aryl or alkenyl radicals and n is a number greater than 100;

esterified fatty acid ethoxylates of the general formula R—COO—(—$CH_2$—$CH_2$—O—)$_n$—C(O)—R', where R and R', independently of one another, are branched or unbranched alkyl, aryl or alkenyl radicals and n is a number greater than 100;

polypropylene glycol ethers of the general formula R—O—(—$CH_2$—$CH(CH_3)$—O—)$_n$—R', where R and R', independently of one another, are branched or unbranched alkyl, aryl or alkenyl radicals and n is a number greater than 100;

esterified fatty acid propoxylates of the general formula R—COO—(—$CH_2$—$CH(CH_3)$—O—)$_n$—C(O)—R', where R and R', independently of one another, are branched or unbranched alkyl, aryl or alkenyl radicals and n is a number greater than 100;

polypropylene glycol ethers of the general formula R—O—$X_n$—$Y_m$—R', where R and R', independently of one another, are branched or unbranched alkyl, aryl or alkenyl radicals, where X and Y are not identical and in each case are either an oxyethylene group or an oxypropylene group and n and m, independently of one another, are numbers whose sum is greater than 100;

etherified fatty acid propoxylates of the general formula R—COO—$X_n$—$Y_m$—R', where R and R', independently of one another, are branched or unbranched alkyl, aryl or alkenyl radicals, where X and Y are not identical and are in each case either an oxyethylene group or an oxypropylene group and n and m, independently of one another, are numbers whose sum is greater than 100.

PEG-150 distearate, PEG 800 distearate, PEG 800 $Chol_2$ and PEG-150 dioleate are particularly advantageous. PEG-300 pentaerythrityl tetraisostearate, PEG-120 methylglucose dioleate, PEG-160 sorbitan triisostearate, PEG-450 sorbitol hexaisostearate and PEG-230 glyceryl triisostearate are to be used advantageously as crosslinkers. In addition, PEG-200 glyceryl palmitate is also suitable. In addition, the crosslinker from Südchemie with the name Purethix 1442 (polyether-1) is also advantageous. It is also possible to use polyurethane crosslinkers, such as Rheolate 204, 205, 208 (Rheox) or cosmetic variants modified therefrom or DW 1206B from Rhom & Haas or Serad Fx 1010, 1035 from Hüls. In addition, it is also advantageous to use mixtures of the polymers described above, for example of PEG 800 distearate and PEG-800 $Chol_2$.

A slightly modified way of forming emulsions according to the invention comprises in immobilizing the oil droplets through the use of hydrophobically modified, synthetic or natural polymers. Such polymers are sometimes also referred to as associative thickeners.

In FIGS. 1 and 2, lines show the backbone of a water-soluble or water-dispersible crosslinker, where the branching points represent hydrophobic groups bonded covalently to the polymer, symbolized here by rectangles. The hydrophobic radicals can position themselves next to each other as a result of hydrophobic interaction. Emulsion droplets can likewise position themselves at the crosslinking points as a result of hydrophobic interactions. In this connection, it is essentially unimportant whether the hydrophobic radicals "dip in" or whether the hydrophobic radicals are in merely superficial contact with the emulsion droplets and adhere to these to a greater or lesser degree.

It is accordingly also advantageous, particularly when the crosslinker or the crosslinkers are to be chosen from the group of associative thickeners, to choose hydrophobically substituted polysaccharide derivatives, for example hydrophobically substituted cellulose ethers, hydrophobically substituted starches, alginates, glucans, chitins, dextrans, caseinates, pectins, proteins and gums, and also polyurethanes, polyacrylamides, polyvinyl alcohols, polyacrylates, water-soluble silicone polymers and the like. For example, cetylhydroxyethylcellulose can be used advantageously.

In some instances, it may also be advantageous if the crosslinker or crosslinkers used according to the invention has or have physiological effectiveness in the sense of a cosmetic or pharmaceutical effect. Thus, for example, the biosurfactant esters disclosed in German laid-open specification 43 44 661 can be used advantageously for the purposes of the present invention.

In addition, combinations of the above-described crosslinkers with classic polymers which are not able to crosslink due to their structure are also possible, which are referred to below as thickeners. Inorganic thickeners can also be used.

The inorganic thickener or thickeners can, for example, be chosen advantageously from the group of modified or unmodified, naturally occurring or synthetic sheet silicates. Very advantageous inorganic gel formers for the purposes of the present invention are aluminum silicates, such as the montmorillonites (bentonites, hectorites and derivatives thereof, such as quaternium-18 bentonite, quaternium-18 hectorite, stearalkonium bentonite and stearalkonium hectorite), but also magnesium aluminum silicates (Veegum® grades) and sodium magnesium silicates (Laponite® grades). Bentone® is a trade name for various neutral and chemically inert gelling agents which are constructed from long-chain, organic ammonium salts and specific montmorillonite grades.

The group of cosmetically and dermatologically relevant hydrocolloids may, for example, be:

organic, natural compounds, such as, for example, agar agar, carrageen, tragacanth, gum arabic, alginates, pectins, polyoses, guar flour, carob bean flour, starch, dextrins, gelatin, casein;

organic, modified natural substances, such as, for example, carboxymethylcellulose and other cellulose ethers, hydroxyethylcellulose and hydroxypropylcellulose and microcrystalline cellulose the like;

organic, completely synthetic compounds, such as, for example, polyacrylic and polymethacrylic compounds, vinyl polymers, polycarboxylic acids, polyethers, polyimines, polyamides, polyurethanes; and inorganic compounds, such as, for example, polysilicic acids, clay minerals, such as montmorillonites, zeolites, silicas;

Further hydrocolloids which are advantageous according to the invention are, for example, methylcelluloses, which is the term used for the methyl ethers of cellulose. They are characterized by the following structural formula:

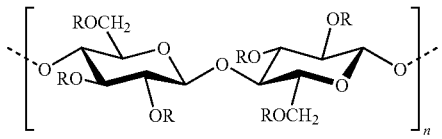

in which R may be a hydrogen or a methyl group.

Particularly advantageous for the purposes of the present invention are the cellulose mixed ethers, which are generally likewise referred to as methylcelluloses, which contain, besides a predominating content of methyl groups, additionally 2-hydroxyethyl groups, 2-hydroxypropyl groups or 2-hydroxybutyl groups. Particular preference is given to (hydroxypropyl)methylcelluloses, for example those available under the trade name Methocel® E4M from Dow Chemical Comp.

Also advantageous according to the invention is sodium carboxymethylcellulose, the sodium salt of the glycolic ether of cellulose, for which R in structural formula I may be a hydrogen or $CH_2$—COONa. Particular preference is given to the sodium carboxymethylcellulose available under the trade name Natrosol Plus 330 CS from Aqualon and also referred to as cellulose gum.

Also preferred for the purposes of the present invention is xanthan (CAS No. 11138-66-2), also called xanthan gum, which is an anionic heteropolysaccharide which is usually formed by fermentation from corn sugar and is isolated as the potassium salt. It is produced by Xanthomonas campestris and a few other species under aerobic conditions and has a molecular weight of from $2 \times 10^6$ to $24 \times 10^6$. Xanthan is formed from a chain having β-1,4-bonded glucose (cellulose) with side chains. The structure of the subgroups consists of glucose, mannose, glucuronic acid, acetate and pyruvate. Xanthan is the name given to the first microbial anionic heteropolysaccharide. It is produced by Xanthomonas campestris and a few other species under aerobic conditions and has a molecular weight of 2-15 $10^6$. Xanthan is formed from a chain having β-1,4-bonded glucose (cellulose) with side chains. The structure of the subgroups consists of glucose, mannose, glucuronic acid, acetate and pyruvate. The number of pyruvate units determines the viscosity of the xanthan. Xanthan is produced in two-day batch cultures with a yield of 70 to 90%, based on carbohydrate used. In this connection, yields of 25 to 30 g/l are achieved. After the culture has been destroyed, work-up takes place by precipitation with, for example, 2-propanol. Xanthan is then dried and ground.

An advantageous gel former for the purposes of the present invention is also carrageen, a gel-forming extract with a similar structure to agar, from north Atlantic red algae, which belong to the Florideae (*Chondrus crispus* and *Gigartina stellata*). The term carrageen is frequently used for the dried algae product and carrageenan for the extract thereof. The carrageen precipitated from the hot water extract of the algae is a colorless to sand-colored powder with a molecular weight range from 100 000 to 800 000 and a sulfate content of about 25%. Carrageen, which is very readily soluble in warm water, forms a thixotropic gel upon cooling, even if the water content is 95 to 98%. The rigidity of the gel is effected by the double helix structure of carrageen. In the case of carrageenan three main constituents are differentiated: the gel-forming κ fraction consists of D-galactose 4-sulfate and 3,6-anhydro-α-D-galactose, which has alternate glycoside bonds in the 1,3- and 1,4-position (by contrast, agar contains 3,6-anhydro-α-L-galactose). The nongelling λ fraction is composed of 1,3-glycosidically linked D-galactose 2-sulfate and 1,4-bonded D-galactose 2,6-disulfate radicals, and is readily soluble in cold water. ι-Carrageenan, composed of D-galactose 4-sulfate in 1,3 bond and 3,6-anhydro-α-D-galactose 2-sulfate in 1,4 bond, is both water-soluble and also gel-forming. The type of cations present ($K^+$, $NH_4^+$, $Na^+$, $Mg^{2+}$, $Ca^{2+}$) also influences the solubility of the carrageens.

The use of chitosan in cosmetic preparations is known per se. Chitosan represents a partially deacylated chitin. This biopolymer has, inter alia, film-forming properties and is characterized by a silky feel on the skin. A disadvantage, however, is its severe stickiness on the skin which occurs in particular—temporarily—during application. In individual cases, corresponding preparations may not then be marketable since they are unacceptable to or viewed negatively by the consumer. As is known, chitosan is used, for example, in hair care. It is suitable, to a better degree than the chitin on which it is based, as a thickener or stabilizer and improves the adhesion and water resistance of polymeric films. A representative of a large number of literature references for the prior art is: H. P. Fiedler, "Lexikon der Hilfsstoffe für Pharmazie, Kosmetik und angrenzende Gebiete" [Lexicon of Auxiliaries for Pharmacy, Cosmetics and Related Fields], third edition 1989, Editio Cantor, Aulendorf, p. 293, keyword "chitosan".

It is advantageous to choose chitosans with molecular weights between 10 000 and 1 000 000, in particular those with molecular weights between 100 000 and 1 000 000 [determined by means of gel permeation chromatography].

Polyacrylates are gelling agents likewise to be used advantageously for the purposes of the present invention. Polyacrylates advantageous according to the invention are acrylate-alkyl acrylate copolymers, in particular those chosen from the group of so-called carbomers or carbopols (Carbopol® is actually a registered trademark of B.F. Goodrich Company). In particular, the acrylate-alkyl acrylate copolymer or copolymers advantageous according to the invention are characterized by the following structure:

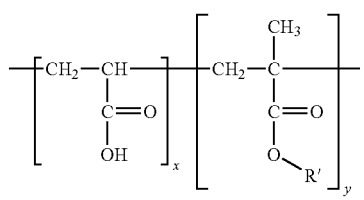

where R' is a long-chain alkyl radical, and x and y represent numbers which symbolize the respective stoichiometric portion of each of the comonomers.

According to the invention, particular preference is given to acrylate copolymers and acrylate-alkyl acrylate copolymers which are available under the trade names Carbopol® 1382, Carbopol® 981 and Carbopol® 5984 from B.F. Goodrich Company, preference being given to polyacrylates from the group of carbopol grades 980, 981, 1382, 2984, 5984, and particular preference being given to Carbomer 2001.

Also advantageous are copolymers of $C_{10-30}$-alkylacrylates and one or more monomers of acrylic acid, of methacrylic acid or esters thereof which are crosslinked with an allyl ether of sucrose or an allyl ether of pentaerythritol.

Compounds which bear the INCI name "Acrylates/$C_{10-30}$ Alkyl Acrylate Crosspolymer" are advantageous. Particularly advantageous are those polymers available under the trade names Pemulen TR1 and Pemulen TR2 from B.F. Goodrich Company. Compounds which bear the INCI name ammonium acryloyldimethyl-taurates/vinylpyrrolidone copolymers are advantageous. According to the invention, the ammonium acryloyldimethyltaurates/vinylpyrrolidone copolymer or copolymers advantageously have the empirical formula $[C_7H_{16}N_2SO_4]_n[C_6H_9NO]_m$, which corresponds to the following statistical structure

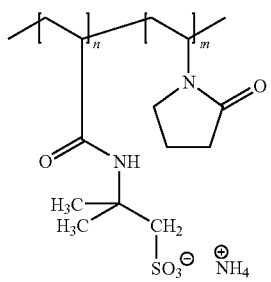

Preferred species for the purposes of the present invention are listed in the Chemical Abstracts under the registry numbers 58374-69-9, 13162-05-5 and 88-12-0 and are available under the trade name Aristoflex® AVC from Clariant GmbH. Also advantageous are copolymers/crosspolymers comprising acryloyldimethyl taurate, such as, for example, Simugel® EG or Simugel® EG from Seppic S.A.

Further hydrocolloids to be used advantageously according to the invention are also 1. Water-soluble or -dispersible anionic polyurethanes which are advantageously obtainable from
i) at least one compound which contains two or more active hydrogen atoms per molecule,
ii) at least one diol containing acid or salt groups and
iii) at least one diisocyanate.

Component i) is in particular diols, aminoalcohols, diamines, polyesterols, polyetherols with a number-average molecular weight of in each case up to 3000 or mixtures thereof, where up to 3 mol % of said compounds may be replaced by triols or triamines. Preference is given to diols and polyesterdiols. In particular, the component (a) comprises at least 50% by weight, based on the total weight of component (a), of a polyesterdiol. Suitable polyesterdiols are all those which are customarily used for the preparation of polyurethanes, in particular reaction products of phthalic acid and diethylene glycol, isophthalic acid and 1,4-butanediol, isophthalic acid/adipic acid and 1,6-hexanediol, and adipic acid and ethylene glycol or 5-NaSO$_3$-isophthalic acid, phthalic acid, adipic acid and 1,6-hexanediol.

Diols which can be used are, for example, ethylene glycol, propylene glycol, butylene glycol, neopentyl glycol, polyetherols, such as polyethylene glycols with molecular weights up to 3000, block copolymers of ethylene oxide and propylene oxide with number-average molecular weights of up to 3000 or block copolymers of ethylene oxide, propylene oxide and butylene oxide which contain the copolymerized alkylene oxide units in random distribution or in the form of blocks. Preference is given to ethylene glycol, neopentyl glycol, di-, tri-, tetra-, penta- or hexaethylene glycol. Diols which can be used are also poly(☐-hydroxycarboxylic acid) diols.

Suitable aminoalcohols are, for example, 2-aminoethanol, 2-(N-methylamino)ethanol, 3-aminopropanol or 4-aminobutanol.

Suitable diamines are, for example, ethylenediamine, propylenediamine, 1,4-diaminobutane and 1,6-diaminohexane, and also α,ω-diamines which can be prepared by amination of polyalkylene oxides with ammonia.

Component ii) is, in particular, dimethylolpropanoic acid or compounds of the formulae:

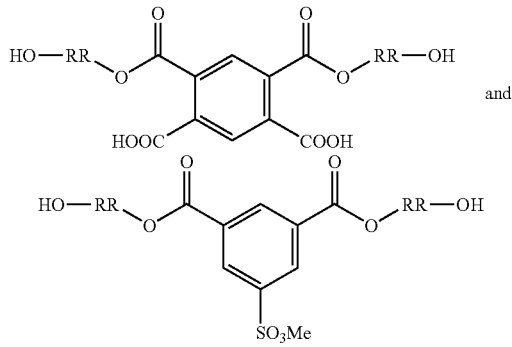

where RR is in each case a $C_2$-$C_{18}$-alkylene group and Me is Na or K.

Component iii) is in particular hexamethylene diisocyanate, isophorone diisocyanate, methyldiphenyl isocyanate (MDI), or tolylene diisocyanate. calculated, in which: $\eta_r$=relative viscosity (dynamic viscosity of the solution/dynamic viscosity of the solvent) and c=mass concentration of polymer in the solution (in g/cm$^3$).

2. Water-soluble or -dispersible cationic polyurethanes and polyureas of
a) at least one diisocyanate, which may have already been reacted beforehand with one or more compounds which contain two or more active hydrogen atoms per molecule, and
b) at least one diol, primary or secondary aminoalcohol, primary or secondary diamine or primary or secondary triamine with one or more tertiary, quaternary or protonated tertiary amino nitrogen atoms.

Preferred diisocyanates are as given above under 1). Compounds with two or more active hydrogen atoms are diols, aminoalcohols, diamines, polyesterols, polyamidediamines and polyetherols. Suitable compounds of this type are as given above under 1).

The polyurethanes are prepared as described above under 1). Charged cationic groups can be produced in the polyureas from the tertiary amino nitrogen atoms present either by protonation, e.g. with carboxylic acids such as lactic acid, or by quaternization, e.g. with alkylating agents, such as $C_1$- to $C_4$-alkyl halides or sulfates. Examples of such alkylating agents are ethyl chloride, ethyl bromide, methyl chloride, methyl bromide, dimethyl sulfate and diethyl sulfate.

These polymers and their preparation are described in more detail in DE-A42 41 118, to the entire scope of which reference is hereby made.

3. Linear polyurethanes with carboxylate groups from
i) a 2,2-hydroxymethyl-substituted carboxylic acid of the formula:

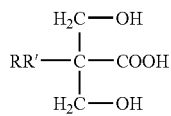

in which RR' is a hydrogen atom or a $C_1$-$C_{20}$-alkyl group, which is used in an amount which suffices for 0.35 to 2.25 milliequivalents of carboxyl groups to be present in the polyurethane per g of polyurethane,
ii) 10 to 90% by weight, based on the weight of the polyurethane, of one or more organic compounds with not more than two active hydrogen atoms and
iii) one or more organic diisocyanates.

The carboxyl groups present in the polyurethane are, finally, at least partially neutralized with a suitable base. These polymers and their preparation are described in EP-A-619 111, to the entire scope of which reference is hereby made.

4. Carboxyl-containing polycondensation products of anhydrides of tri- or tetracarboxylic acids and diols, diamines or aminoalcohols (polyesters, polyamides or polyester amides). These polymers and their preparation are described in more detail in DE-A42 24 761, to the entire scope of which reference is hereby made.

5. Polyacrylates and polymethacrylates, as are described in more detail in DE-A43 14 305, 36 27 970 and 29 17 504. Reference is hereby made to these publications in their entirety.

The total amount of one or more hydrocolloids in the finished cosmetic or dermatological preparations is advantageously chosen to be less than 5% by weight, preferably between 0.01 and 1.0% by weight, based on the total weight of the preparations.

The preparations according to the invention can advantageously in each case comprise 0.001 to 20% by weight of one or more crosslinkers and non-crosslinking thickeners used according to the invention. Preferably, the content of thickeners and crosslinkers is chosen in each case to be from 0.01 to 10% by weight, in particular 0.1 to 5% by weight, in each case based on the total weight of the preparations.

The oils and fats customary in cosmetics can be used as oil phase. The process according to the invention permits the preparation of finely divided emulsions with a large number of typical oil phases: ethers (dicaprylyl ether), carbonates (dicaprylyl carbonate), butylene glycol esters (butylene glycol caprylate, caprate), tartaric esters (Di-C12-13 alkyl tartrate), succinates (caprylic/capric diglyceryl succinate), triglycerides (caprylic/capric triglyceride), alcohols (octyldodecanol), ester oils (cetearyl isononanoate), glycerides (cocoglyceride), hydrocarbons (mineral oil, hydrogenated polydecene, isoeicosane, dioctylcyclohexane, squalane, squalene), silicone oils (cyclomethicone) and mixtures of these oil phases.

In addition, waxes may also be a constituent of the oil phase, such as, for example, methyl palmitate, cetyl palmitate, $C_{20-40}$-alkyl stearate, $C_{18-36}$-acid triglyceride.

For the preparations according to the invention, the following quantitative percentages by weight, in each case based on the total weight of the preparations, are preferred:

| | |
|---|---|
| O/W emulsifier: | 0.01-60%, in particular 0.1-10% |
| W/O emulsifier: | 0.1-60%, in particular 0.1-10% |
| Oil phase: | 0.01-50%, in particular 0.1-30% |
| Additives for the oil phase: | 0.01-20%, in particular 0.1-15% |
| Additives for the water phase: | 0.01-80%, in particular 0.1-60% |
| Crosslinker | 0.01-20%, in particular 0.1-10% |
| Thickener (noncrosslinking): | 0.01-20%, in particular 0.1-10% |
| Water | ad 100% |

Particularly advantageous for the purposes of the present invention are crosslinked systems based on emulsions of the oil-in-water type which comprise:

a discontinuous oil phase and a continuous water phase optionally comprising at least one W/O emulsifier comprising at least one O/W emulsifier where the O/W emulsifier or the O/W emulsifiers is or are chosen advantageously from the group:

of fatty alcohol ethoxylates of the general formula R—O—(—$CH_2$—$CH_2$—O—)$_n$—H, where R is a branched or unbranched alkyl, aryl or alkenyl radical and n is a number from 10 to 50;

ethoxylated/propoxylated wool wax alcohols;

polyethylene glycol ethers of the general formula R—O—(—$CH_2$—$CH_2$—O—)$_n$—R', where R and R', independently of one another, are branched or unbranched alkyl or alkenyl radicals and n is a number from 10 to 80;

fatty acid ethoxylates of the general formula R—COO—(—$CH_2$—$CH_2$—O—)$_n$—H, where R is a branched or unbranched alkyl or alkenyl radical and n is a number from 10 to 40;

etherified fatty acid ethoxylates of the general formula R—COO—(—$CH_2$—$CH_2$—O—)$_n$—R', where R and R', independently of one another, are branched or unbranched alkyl or alkenyl radicals and n is a number from 10 to 80;

esterified fatty acid ethoxylates of the general formula R—COO—(—$CH_2$—$CH_2$—O—)$_n$—C(O)—R', where R and R', independently of one another, are branched or unbranched alkyl or alkenyl radicals and n is a number from 10 to 80;

polyethylene glycol glycerol fatty acid esters of saturated or unsaturated, branched or unbranched fatty acids and a degree of ethoxylation between 3 and 50;

ethoxylated sorbitan esters with a degree of ethoxylation of from 3 to 100;

cholesterol ethoxylates with a degree of ethoxylation between 3 and 50;

ethoxylated triglycerides with a degree of ethoxylation between 3 and 150;

of alkyl ether carboxylic acids of the general formula R—O—(—CH$_2$—CH$_2$—O—)$_n$—CH$_2$—COOH or cosmetically or pharmaceutically acceptable salts thereof, where R is a branched or unbranched alkyl or alkenyl radical having 5 to 30 carbon atoms and n is a number from 5 to 30;

polyoxyethylene sorbitol fatty acid esters based on branched or unbranched alkanoic or alkenoic acids and having a degree of ethoxylation of from 5 to 100, for example of the sorbeth type;

of alkyl ether sulfates or the acids on which these sulfates are based of the general formula R—O—(—CH$_2$—CH$_2$—O—)$_n$—SO$_3$—H with cosmetically or pharmaceutically acceptable cations, where R is a branched or unbranched alkyl or alkenyl radical having 5 to 30 carbon atoms and n is a number from 1 to 50;

fatty alcohol propoxylates of the general formula R—O—(—CH$_2$—CH(CH$_3$)—O—)$_n$—H, where R is a branched or unbranched alkyl or alkenyl radical and n is a number from 10 to 80;

polypropylene glycol ethers of the general formula R—O—(—CH$_2$—CH(CH$_3$)—O—)$_n$—R', where R and R', independently of one another, are branched or unbranched alkyl or alkenyl radicals and n is a number from 10 to 80;

etherified fatty acid propoxylates of the general formula R—COO—(—CH$_2$—CH(CH$_3$)—O—)$_n$—R', where R and R', independently of one another, are branched or unbranched alkyl or alkenyl radicals and n is a number from 10 to 80;

of esterified fatty acid propoxylates of the general formula R—COO—(—CH$_2$—CH(CH$_3$)—O—)$_n$—C(O)R', where R and R', independently of one another, are branched or unbranched alkyl or alkenyl radicals and n is a number from 10 to 80;

fatty acid propoxylates of the general formula R—COO—(—CH$_2$—CH(CH$_3$)—O—)$_n$—H, where R is a branched or unbranched alkyl or alkenyl radical and n is a number from 10 to 80;

polypropylene glycol glycerol fatty acid esters of saturated or unsaturated, branched or unbranched fatty acids and having a degree of propoxylation between 3 and 80 propoxylated sorbitan esters having a degree of propoxylation from 3 to 100;

cholesterol propoxylates having a degree of propoxylation from 3 to 100;

propoxylated triglycerides having a degree of propoxylation from 3 to 100;

alkyl ether carboxylic acids of the general formula R—O—(—CH$_2$—CH(CH$_3$)—O—)$_n$—CH$_2$—COOH, or cosmetically or pharmaceutically acceptable salts thereof, where R is a branched or unbranched alkyl or alkenyl radical and n is a number from 3 to 50;

alkyl ether sulfates or the acids on which these sulfates are based of the general formula R—O—(—CH$_2$—CH(CH$_3$)—O—)$_n$—SO$_3$—H with cosmetically or pharmaceutically acceptable cations, where R is a branched or unbranched alkyl or alkenyl radical having 5 to 30 carbon atoms and n is a number from 1 to 50;

fatty alcohol ethoxylates/propoxylates of the general formula R—O—X$_n$—Y$_m$—H, where R is a branched or unbranched alkyl or alkenyl radical, where X and Y are not identical and are in each case either an oxyethylene group or an oxypropylene group and n and m, independently of one another, are numbers from 5 to 50;

polypropylene glycol ethers of the general formula R—O—X$_n$—Y$_m$—R', where R and R', independently of one another, are branched or unbranched alkyl or alkenyl radicals, where X and Y are not identical and are in each case either an oxyethylene group or an oxypropylene group and n and m, independently of one another, are numbers from 5 to 100;

etherified fatty acid propoxylates of the general formula R—COO—X$_n$—Y$_m$—R', where R and R', independently of one another, are branched or unbranched alkyl or alkenyl radicals, where X and Y are not identical and in each case are either an oxyethylene group or an oxypropylene group and n and m, independently of one another, are numbers from 5 to 100;

fatty acid ethoxylates/propoxylates of the general formula R—COO—X$_n$—Y$_m$—H, where R is a branched or unbranched alkyl or alkenyl radical, where X and Y are not identical and are in each case either an oxyethylene group or an oxypropylene group and n and m, independently of one another, are numbers from 5 to 50;

polyglycerol methyl glucose esters of saturated or unsaturated, branched or unbranched alkanecarboxylic acids or hydroxycarboxylic acids with a chain length of 8 to 24, in particular 12 to 18, carbon atoms;

glycerol fatty acid citrates;

water-dispersible silicone emulsifiers;

polyglycerol esters (saturated and unsaturated) with a chain length of 8 to 24, in particular 12 to 18, carbon atoms.

The W/O emulsifiers (one or more), which are present if desired, can preferably be chosen from the group of fatty alcohol ethoxylates of the general formula R—O—(—CH$_2$—CH$_2$—O—)$_n$—H, where R is a branched or unbranched alkyl, aryl or alkenyl radical and n is a number from 1 to 10;

polyethylene glycol ethers of the general formula R—O—(—CH$_2$—CH$_2$—O—)$_n$—R', where R and R', independently of one another, are branched or unbranched alkyl or alkenyl radicals and n is a number from 1 to 30;

fatty acid ethoxylates of the general formula R—COO—(—CH$_2$—CH$_2$—O—)$_n$—H, where R is a branched or unbranched alkyl or alkenyl radical and n is a number from 1 to 20;

esterified fatty acid ethoxylates of the general formula R—COO—(—CH$_2$—CH$_2$—O—)$_n$—C(O)—R', where R and R', independently of one another, are branched or unbranched alkyl or alkenyl radicals and n is a number from 1 to 20;

esterified fatty acid ethoxylates of the general formula R—COO—(—CH$_2$—CH$_2$—O—)$_n$—C(O)—R', where R and R', independently of one another, are branched or unbranched alkyl, hydroxyalkyl or alkenyl radicals and n is a number from 1 to 40;

etherified fatty acid ethoxylates of the general formula R—COO—(—CH$_2$—CH$_2$—O—)$_n$—R', where R and R', independently of one another, are branched or unbranched alkyl or alkenyl radicals and n is a number from 1 to 40;

fatty alcohol propoxylates of the general formula R—O—(—CH$_2$—CH(CH$_3$)—O—)$_n$—H, where R is a branched or unbranched alkyl or alkenyl radical and n is a number from 1 to 30;

polyoxyethylene sorbitan fatty acid esters based on branched or unbranched alkanoic or alkenoic acids and having a degree of ethoxylation of from 1 to 10;

cholesterol ethoxylates having a degree of ethoxylation between 1 and 10;

ethoxylated glycerides having a degree of ethoxylation of from 1 to 30;

ethoxylated triglycerides having a degree of ethoxylation between 1 and 30;

monoglycerol ethers of the type R—O—CH$_2$—C(H)OH—CH$_2$OH, where R is a branched or unbranched alkyl, aryl or alkenyl radical;

monoglycerol esters of the type RC(O)OCH$_2$—C(H)OH—CH$_2$OH, where R is a branched or unbranched alkyl, hydroxyalkyl, aryl or alkenyl radical;

diglycerol esters of the type RC(O)OCH$_2$—C(H)OH—CH$_2$OC(O)R', where R and R', independently of one another, are branched or unbranched alkyl, hydroxyalkyl or alkenyl radicals and n is a number from 1 to 30;

polyglycerolmono- or di- or polyesters, where the fatty acids, independently of one another, are branched or unbranched alkyl, hydroxyalkyl or alkenyl radicals;

pentaerythritol esters, where the fatty acids, independently of one another, are branched or unbranched alkyl, hydroxyalkyl or alkenyl radicals;

propylene glycol esters, where the fatty acids, independently of one another, are branched or unbranched alkyl, hydroxyalkyl or alkenyl radicals;

sorbitan esters, where the fatty acids, independently of one another, are branched or unbranched alkyl, hydroxyalkyl or alkenyl radicals;

fatty alcohols R—OH and fatty acids RCOOH, where R is a branched or unbranched alkyl or alkenyl radical;

silicone emulsifiers, such as, for example, dimethicone copolyol, alkyl dimethicone copolyol (cetyl dimethicone copolyol), alkyl methicone copolyols (lauryl methicone copolyol), octyl dimethicone ethoxy glucoside; and methylglucose esters, where the fatty acids, independently of one another, are branched or unbranched alkyl, hydroxyalkyl or alkenyl radicals.

The total emulsifier content is preferably 0.01 to 20% by weight, based on the total weight of the preparation.

In particular, it is advantageous if the O/W emulsifier or the O/W emulsifiers is or are chosen from the group of:

fatty alcohol ethoxylates of the general formula R—O—(—CH$_2$—CH$_2$—O—)$_n$—H, where R is a branched or unbranched alkyl or alkenyl radical having 5 to 30 carbon atoms and n is a number from 10 to 25;

ethoxylated/propoxylated wool wax alcohols with HLB values of 11-16;

polyethylene glycol ethers of the general formula R—O—(—CH$_2$—CH$_2$—O—)$_n$—R', where R and R', independently of one another, are branched or unbranched alkyl or alkenyl radicals having 5 to 30 carbon atoms and n is a number from 10 to 25;

fatty acid ethoxylates of the general formula R—COO—(—CH$_2$—CH$_2$—O—)$_n$—H, where R is a branched or unbranched alkyl or alkenyl radical having 5 to 30 carbon atoms and n is a number from 10 to 25;

etherified fatty acid ethoxylates of the general formula R—COO—(—CH$_2$—CH$_2$—O—)$_n$—R', where R and R', independently of one another, are branched or unbranched alkyl or alkenyl radicals having 5 to 30 carbon atoms and n is a number from 10 to 50;

esterified fatty acid ethoxylates of the general formula R—COO—(—CH$_2$—CH$_2$—O—)$_n$—C(O)—R', where R and R', independently of one another, are branched or unbranched alkyl or alkenyl radicals having 5 to 30 carbon atoms and n is a number from 10 to 50;

polyethylene glycol glycerol fatty acid esters of saturated or unsaturated, branched or unbranched fatty acids having 6 to 26 carbon atoms and a degree of ethoxylation between 3 and 40;

ethoxylated sorbitan esters with a degree of ethoxylation of from 3 to 30;

cholesterol ethoxylates with HLB values of 11 to 16;

ethoxylated triglycerides with HLB values of 11 to 16;

alkyl ether carboxylic acids of the general formula R—O—(—CH$_2$—CH$_2$—O—)$_n$—CH$_2$—COOH or cosmetically or pharmaceutically acceptable salts thereof, where R is a branched or unbranched alkyl or alkenyl radical having 5 to 30 carbon atoms and n is a number from 10 to 20;

polyoxyethylene sorbitol fatty acid esters based on branched or unbranched alkanoic or alkenoic acids and having a degree of ethoxylation of from 10 to 80, for example of the sorbeth type;

alkyl ether sulfates or the acids on which these sulfates are based of the general formula R—O—(—CH$_2$—CH$_2$—O—)$_n$—SO$_3$—H with cosmetically or pharmaceutically acceptable cations, where R is a branched or unbranched alkyl or alkenyl radical having 5 to 30 carbon atoms and n is a number from 3 to 30;

fatty alcohol propoxylates of the general formula R—O—(—CH$_2$—CH(CH$_3$)—O—)$_n$—H, where R is a branched or unbranched alkyl or alkenyl radical having 5 to 30 carbon atoms and n is a number from 10 to 30;

polypropylene glycol ethers of the general formula R—O—(—CH$_2$—CH(CH$_3$)—O—)$_n$—R', where R and R', independently of one another, are branched or unbranched alkyl or alkenyl radicals having 5 to 30 carbon atoms and n is a number from 10 to 40;

fatty acid propoxylates of the general formula R—COO—(—CH$_2$—CH(CH$_3$)—O—)$_n$—H, where R is a branched or unbranched alkyl or alkenyl radical having 5-30 carbon atoms and n is a number from 10 to 40;

etherified fatty acid propoxylates of the general formula R—COO—(—CH$_2$—CH(CH$_3$)—O—)$_n$—R', where R and R', independently of one another, are branched or unbranched alkyl or alkenyl radicals having 5 to 30 carbon atoms and n is a number from 10 to 30;

esterified fatty acid propoxylates of the general formula R—COO—(—CH$_2$—CH(CH$_3$)—O—)$_n$—C(O)—R', where R and R', independently of one another, are branched or unbranched alkyl or alkenyl radicals having 5 to 30 carbon atoms and n is a number from 10 to 50;

polypropylene glycol glycerol fatty acid esters of saturated or unsaturated, branched or unbranched fatty acids having 6 to 26 carbon atoms and a degree of propoxylation between 3 and 50;

propoxylated sorbitan esters having a degree of propoxylation from 3 to 80;

cholesterol propoxylates with HLB values of 11 to 16;

propoxylated triglycerides with HLB values of 11 to 16;

alkyl ether carboxylic acids of the general formula R—O—(—CH$_2$—CH(CH$_3$)—O—)$_n$—CH$_2$—COOH or cosmetically or pharmaceutically acceptable salts thereof, where R is a branched or unbranched alkyl or alkenyl radical having 5 to 30 carbon atoms and n is a number from 10 to 30;

alkyl ether sulfates or the acids on which these sulfates are based of the general formula R—O—(—CH$_2$—CH(CH$_3$)—O—)$_n$—SO$_3$—H with cosmetically or pharmaceutically acceptable cations, where R is a branched or unbranched alkyl or alkenyl radical having 5 to 30 carbon atoms and n is a number from 1 to 30;

polyglycerol methyl glucose esters of the type polyglyceryl-3 methyl glucose distearate;

glycerol fatty acid citrates of the type glyceryl stearate citrate; and water-dispersible silicone emulsifiers of the type bis PEG/PPG-16/16 PEG/PPG16/16 dimethicone+caprylic/capric triglyceride (Abil Care 85).

According to the invention, the ethoxylated O/W emulsifiers used are particularly advantageously chosen from the group of substances with HLB values of 11 to 16 if the O/W emulsifiers have saturated radicals R and R'. If the O/W emulsifiers have unsaturated radicals R or R', or if isoalkyl derivatives are present, then the preferred HLB value of such emulsifiers may also be lower or higher.

It is advantageous to choose the fatty alcohol ethoxylates from the group of ethoxylated stearyl alcohols, cetyl alcohols, cetylstearyl alcohols (cetearyl alcohols). Particular preference is given to:

polyethylene glycol(13) stearyl ether (steareth-13), polyethylene glycol(14) stearyl ether (steareth-14), polyethylene glycol(15) stearyl ether (steareth-15), polyethylene glycol(16) stearyl ether (steareth-16), polyethylene glycol(17) stearyl ether (steareth-17), polyethylene glycol(18) stearyl ether (steareth-18), polyethylene glycol(19) stearyl ether (steareth-19), polyethylene glycol(20) stearyl ether (steareth-20), steareth-21, polyethylene glycol(12) isostearyl ether (isosteareth-12), polyethylene glycol(13) isostearyl ether (isosteareth-13), polyethylene glycol(14) isostearyl ether (isosteareth-14), polyethylene glycol(15) isostearyl ether (isosteareth-15), polyethylene glycol(16) isostearyl ether (isosteareth-16), polyethylene glycol(17) isostearyl ether (isosteareth-17), polyethylene glycol(18) isostearyl ether (isosteareth-18), polyethylene glycol(19) isostearyl ether (isosteareth-19), polyethylene glycol(20) isostearyl ether (isosteareth-20), polyethylene glycol(13) cetyl ether (ceteth-13), polyethylene glycol(14) cetyl ether (ceteth-14), polyethylene glycol(15) cetyl ether (ceteth-15), polyethylene glycol(16) cetyl ether (ceteth-16), polyethylene glycol(17) cetyl ether (ceteth-17), polyethylene glycol(18) cetyl ether (ceteth-18), polyethylene glycol(19) cetyl ether (ceteth-19), polyethylene glycol(20) cetyl ether (ceteth-20), polyethylene glycol(13) isocetyl ether (isoceteth-13), polyethylene glycol(14) isocetyl ether (isoceteth-14), polyethylene glycol(15) isocetyl ether (isoceteth-15), polyethylene glycol(16) isocetyl ether (isoceteth-16), polyethylene glycol(17) isocetyl ether (isoceteth-17), polyethylene glycol(18) isocetyl ether (isoceteth-18), polyethylene glycol(19) isocetyl ether (isoceteth-19), polyethylene glycol(20) isocetyl ether (isoceteth-20), polyethylene glycol(12) oleyl ether (oleth-12) polyethylene glycol(13) oleyl ether (oleth-13), polyethylene glycol(14) oleyl ether (oleth-14), polyethylene glycol(15) oleyl ether (oleth-15), polyethylene glycol(12) lauryl ether (laureth-12), polyethylene glycol(12) isolauryl ether (isolaureth-12), polyethylene glycol(13) cetylstearyl ether (ceteareth-13), polyethylene glycol(14) cetylstearyl ether (ceteareth-14), polyethylene glycol(15) cetylstearyl ether (ceteareth-15), polyethylene glycol(16) cetylstearyl ether (ceteareth-16), polyethylene glycol(17) cetylstearyl ether (ceteareth-17), polyethylene glycol(18) cetylstearyl ether (ceteareth-18), polyethylene glycol(19) cetylstearyl ether (ceteareth-19), polyethylene glycol(20) cetylstearyl ether (ceteareth-20).

It is also advantageous to choose the fatty acid ethoxylates from the following group: polyethylene glycol(20) stearate, polyethylene glycol(21) stearate, polyethylene glycol(22) stearate, polyethylene glycol(23) stearate, polyethylene glycol(24) stearate, polyethylene glycol(25) stearate, polyethylene glycol(12). isostearate, polyethylene glycol(13) isostearate, polyethylene glycol(14) isostearate, polyethylene glycol (15) isostearate, polyethylene glycol(16) isostearate, polyethylene glycol(17) isostearate, polyethylene glycol(18) isostearate, polyethylene glycol(19) isostearate, polyethylene glycol(20) isostearate, polyethylene glycol(21) isostearate, polyethylene glycol(22) isostearate, polyethylene glycol (23) isostearate, polyethylene glycol(24) isostearate, polyethylene glycol(25) isostearate, polyethylene glycol(12) oleate, polyethylene glycol(13) oleate, polyethylene glycol (14) oleate, polyethylene glycol(15) oleate, polyethylene glycol(16) oleate, polyethylene glycol(17) oleaie, polyethylene glycol(18) oleate, polyethylene glycol(19) oleate, polyethylene glycol(20) oleate.

The ethoxylated alkyl ether carboxylic acid or salt thereof which can be used is advantageously sodium laureth-11 carboxylate. Sodium laureth-4 sulfate can be used advantageously as alkyl ether sulfate. An advantageous ethoxylated cholesterol derivative which may be used is polyethylene glycol(30) cholesteryl ether. Polyethylene glycol(25) soyasterol has also proven useful.

Ethoxylated triglycerides which can be used advantageously are polyethylene glycol(60) evening primrose glycerides.

It is also advantageous to choose the polyethylene glycol glycerol fatty acid esters from the group consisting of polyethylene glycol(20) glyceryl laurate, polyethylene glycol(21) glyceryl laurate, polyethylene glycol(22) glyceryl laurate, polyethylene glycol(23) glyceryl laurate, polyethylene glycol (6) glyceryl caprate/caprinate, polyethylene glycol(20) glyceryl oleate, polyethylene glycol(20) glyceryl isostearate, polyethylene glycol(18) glyceryl oleate/cocoate.

It is likewise favorable to choose the sorbitan esters from the group consisting of polyethylene glycol(20) sorbitan monolaurate, polyethylene glycol(20) sorbitan monostearate, polyethylene glycol(20) sorbitan monoisostearate, polyethylene glycol(20) sorbitan monopalmitate, polyethylene glycol(20) sorbitan monooleate. Abil Care 85 may be chosen as silicone emulsifier.

W/O emulsifiers which are optional but nevertheless advantageous according to the invention which may be used are: fatty alcohols having 8 to 30 carbon atoms, monoglycerol esters of saturated or unsaturated, branched or unbranched alkanecarboxylic acids or hydroxyalkanecarboxylic acids with a chain length of from 8 to 24, in particular 12 to 18, carbon atoms, diglycerol esters of saturated or unsaturated, branched or unbranched alkanecarboxylic acids or hydroxyalkanecarboxylic acids with a chain length of from 8 to 24, in particular 12 to 18, carbon atoms, monoglycerol ethers of saturated or unsaturated, branched or unbranched alcohols with a chain length of from 8 to 24, in particular 12 to 18, carbon atoms, diglycerol ethers of saturated or unsaturated, branched or unbranched alcohols with a chain length of from 8 to 24, in particular 12 to 18, carbon atoms, propylene glycol esters of saturated or unsaturated, branched or unbranched alkanecarboxylic acids or hydroxyalkanecarboxylic acids with a chain length of from 8 to 24, in particular 12 to 18, carbon atoms, and sorbitan esters of saturated or unsaturated, branched or unbranched alkanecarboxylic acids or hydroxyalkanecarboxylic acids with a chain length of from 8 to 24, in particular 12 to 18, carbon atoms.

Particularly advantageous W/O emulsifiers are glyceryl monostearate, glyceryl monoisostearate, glyceryl linoleate, triglycerol diisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monostearate, sorbitan monolaurate, sorbitan monocaprylate, sucrose distearate, cetyl alcohol, stearyl alcohol, arachidyl alcohol, behenyl alcohol, isobehenyl alcohol, selachyl alcohol, chimyl alcohol, polyethylene glycol(2) stearyl ether (steareth-2), glyceryl monolaurate, glyceryl monocaprinate, glyceryl monocaprylate, polyglyceryl-3 methylglucose distearate, PEG-45/dodecyl glycol copolymer, methoxy-PEG-22-dodecyl glycol copolymer, methylglucose sesquistearate, polyglyceryl-2 dipolyhydroxystearate, cetyl dimethicone copolyols, alkyl methicone copolyols, alkyl dimethicone ethoxy glucosides, PEG-40 sorbitan perisostearate, PEG-30 dipolyhydroxystearate.

According to the invention, it is possible to keep the total content of emulsifiers less than 15% by weight, based on the total weight of the preparations according to the invention. It is preferred to keep the total content of emulsifiers less than 10% by weight, in particular less than 8% by weight, based on the total weight of the preparations.

Skin moisturizers which can be used advantageously are glycerol, chitosan, Fucogel, lactic acid, polyethylene glycol, propylene glycol, dipropylene glycol, butylene glycol, 2-methyl-1,3-propanediol, mannitol, acids such as sodium pyrolidonecarboxylic acid, hyaluronic acid and salts thereof, amino acids and salts thereof such as, for example, glycine, urea, sodium, potassium, magnesium and calcium salts. Glycerol on its own and in combination with one of the abovementioned moisturizers is particularly advantageous.

It can be shown that preparations containing skin-moisturizing ingredients have excellent properties with regard to the moisturization, smoothing and reduction in flakiness of the skin.

The oil phase of the preparations according to the invention is advantageously chosen from the group of esters of saturated or unsaturated, branched or unbranched alkanecarboxylic acids with a chain length of from 3 to 30 carbon atoms and saturated or unsaturated, branched or unbranched alcohols with a chain length of from 3 to 30 carbon atoms, from the group of esters of aromatic carboxylic acids and saturated or unsaturated, branched or unbranched alcohols with a chain length of from 3 to 30 carbon atoms. Such ester oils can then advantageously be chosen from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate, and synthetic, semisynthetic and natural mixtures of such esters, e.g. jojoba oil.

The oil phase can also advantageously be chosen from the group of branched and unbranched hydrocarbons and hydrocarbon waxes, silicone oils, dialkyl ethers, the group of saturated or unsaturated, branched or unbranched alcohols, and fatty acid triglycerides, namely the triglycerol esters of saturated or unsaturated, branched or unbranched alkanecarboxylic acids with a chain length of from 8 to 24, in particular 12 to 18, carbon atoms. The fatty acid triglycerides can, for example, be chosen advantageously from the group of synthetic, semisynthetic and natural oils, e.g. olive oil, sunflower oil, soybean oil, peanut oil, rapeseed oil, almond oil, palm oil, coconut oil, palm kernel oil and the like.

For example, dicaprylyl carbonate, butylene glycol caprylate/caprate, di-C12-13 alkyl tartrate, caprylic/capric diglyceryl succinate, caprylic/capric triglyceride, octyidodecanol, cetearyl isononanoate, cocoglyceride, mineral oil, hydrogenated polydecene, isoeicosane, dioctylcyclohexane, squalane, squalene, $C_{12-15}$-alkyl benzoate and mixtures of these oil phases are advantageous.

Mixtures of $C_{12-15}$-alkyl benzoate and 2-ethylhexyl isostearate, mixtures of $C_{12-15}$-alkyl benzoate and isotridecyl isononanoate, and mixtures of $C_{12-15}$-alkyl benzoate, 2-ethylhexyl isostearate and isotridecyl isononanoate are particularly advantageous.

In addition, waxes may also be a constituent of the oil phase, such as, for example, methyl palmitate, cetyl palmitate, $C_{20-40}$-alkyl stearate, $C_{18-36}$-acid triglyceride. In such cases, the preparations according to the invention can also be produced, if appropriate, as microdispersions of solid wax particles.

Any desired mixtures of such oil and wax components can also be used advantageously for the purposes of the present invention.

The oil phase can advantageously also have a content of cyclic or linear silicone oils or consist entirely of such oils, although it is preferred to use an additional content of other oil phase components apart from the silicone oil or the silicone oils. Cyclomethicone (octamethylcyclotetrasiloxane) is advantageously used as silicone oil to be used according to the invention. However, other silicone oils can also be used advantageously for the purposes of the present invention, for example hexamethylcyclotrisiloxane, polydimethylsiloxane, poly(methylphenylsiloxane).

Mixtures of cyclomethicone and isotridecyl isononanoate, and cyclomethicone and 2-ethylhexyl isostearate are also particularly advantageous.

The preparations according to the invention advantageously comprise electrolytes, in particular one or more salts with the following anions: chlorides, and also inorganic oxo element anions, of these in particular sulfates, carbonates, phosphates, borates and aluminates. Electrolytes based on organic anions can also be used advantageously, for example lactates, acetates, benzoates, propionates, tartrates, citrates and others besides. Comparable effects can also be achieved by ethylenediaminetetraacetic acid and salts thereof.

The cations of the salts used are preferably ammonium, alkylammoniun, alkali metal, alkaline earth metal, magnesium, iron or zinc ions. It goes without saying that only physiologically safe electrolytes should be used in cosmetics. Specific medicinal applications of the microemulsions according to the invention may, on the other hand, at least in principle, necessitate the use of electrolytes which should not be used without medical supervision.

Particular preference is given to sodium and potassium chloride, sodium and potassium bromide, magnesium and calcium chloride, magnesium and calcium bromide, zinc sulfate and mixtures thereof. Salt mixtures as occur in the natural salt of the Dead Sea are likewise advantageous. All of these salts are advantageous since they stimulate endogenous lipid synthesis.

The concentration of the electrolyte or of the electrolytes should be, for example, about 0.1 to 10.0% by weight, particularly advantageously about 0.3 to 8.0% by weight, based on the total weight of the preparation.

The preparations according to the invention also advantageously contribute to skin smoothing, in particular when they are provided with one or more substances which promote skin smoothing.

If the preparations according to the invention are bases for cosmetic deodorants/antiperspirants, then all of the customary active ingredients may be used advantageously, for example odor concealers, such as customary perfume constituents, odor absorbers, for example the sheet silicates described in the patent laid-open specification DE-P 40 09 347, and of these, in particular, montmorillonite, kaolinite, ilite, beidellite, nontronite, saponite, hectorite, bentonite, smectite, and also, for example, zinc salts of ricinoleic acid. Antimicrobial agents are likewise suitable to be incorporated into the microemulsions according to the invention. Advantageous substances are, for example, 2,4,4'-trichloro-2'-hydroxydiphenyl ether (Irgasan), 1,6-di(4-chlorophenylbiguanido)hexane (chlorhexidine), 3,4,4'-trichlorocarbanilide, quaternary ammonium compounds, oil of cloves, mint oil, oil of thyme, triethyl citrate, farnesol (3,7,11-trimethyl-2,6,10-dodecatrien-1-ol), and the active agents described in the patent laid-open specifications DE-37 40 186, DE-39 38 140, DE42 04 321, DE42 29 707, DE42 29 737, DE42 37 081, DE43 09 372, DE-43 24 219.

The customary antiperspirant active ingredients can likewise be used advantageously in the preparations according to the invention, in particular astringents, for example basic aluminum chlorides.

The cosmetic deodorants according to the invention can be in the form of aerosols, i.e. preparations which can be sprayed from aerosol containers, squeezable bottles or by a pump device, or in the form of liquid compositions which can be applied by means of roll-on devices, but also in the form of preparations according to the invention which can be applied from normal bottles and containers.

Suitable propellants for cosmetic deodorants according to the invention which can be sprayed from aerosol containers are the customary known readily volatile, liquefied propellants, for example hydrocarbons (propane, butane, isobutane), which can be used on their own or in a mixture with one another. Compressed air can also be used advantageously.

The person skilled in the art is of course aware that there are propellant gases which are nontoxic per se which would in principle be suitable for the present invention but which nevertheless have to be dispensed with due to an unacceptable impact on the environment or other accompanying circumstances, in particular chlorofluorocarbons (CFCs).

Moreover, it has surprisingly been found that, when using propellants which are soluble in the oil phase, i.e., for example, customary propane/butane mixtures, the preparations according to the invention are not simply sprayed as aerosol droplets, but develop to give finely bubbled, rich foams as soon as such systems containing such propellants experience a pressure release.

Such after-foaming preparations are therefore likewise regarded as being advantageous embodiments of the present invention with an independent inventive step.

When using propellants which are insoluble in the oil phase, the O/W emulsions according to the invention are sprayed as aerosol droplets.

Also favorable are those cosmetic and dermatological preparations which are present in the form of a sunscreen. Preferably, besides the active ingredient combinations according to the invention, these additionally comprise at least one UVA filter substance, at least one UVB filter substance, at least one inorganic pigment, or a combination thereof.

It is, however, also advantageous for the purposes of the present inventions to create those cosmetic and dermatological preparations whose main purpose is not protection against sunlight but which nevertheless have a content of UV protection substances. Thus, for example, UV-A or UV-B filter substances are usually incorporated into day creams.

Preparations according to the invention can advantageously comprise substances which absorb UV radiation in the UVB region, the total amount of the filter substances being, for example, 0.1% by weight to 30% by weight, preferably 0.5 to 10% by weight, in particular 1 to 6% by weight, based on the total weight of the preparations. The UVB filters may be oil-soluble or water-soluble. Examples of oil-soluble substances are:

3-benzylidenecamphor and derivatives thereof, e.g. 3-(4-methylbenzylidene)camphor;

4-aminobenzoic acid derivatives, preferably 2-ethylhexyl 4-(dimethylamino)benzoate, amyl 4-(dimethylamino) benzoate;

esters of cinnamic acid, preferably 2-ethylhexyl 4-methoxycinnamate, isopentyl 4-methoxycinnamate;

esters of salicylic acid, preferably 2-ethylhexyl salicylate, 4-isopropylbenzyl salicylate, homomenthyl salicylate;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably di(2-ethylhexyl) 4-methoxybenzalmalonate;

triazines, such as 2,4,6-trianilino(p-carbo-2'-ethyl-1'-hexyloxy)-1,3,5-triazine, dioctylbutamidotriazone (Uvasorb HEB, Sigma 3V), triazines (triazoles) under the trade name Tinosorb M and S (Ciba), Uvinul T 150 dibenzoylmethane derivatives [for example 4-(tert-butyl)-4'-methoxydibenzoylmethane], 1,4-di(2-oxo-10-sulfo-3-bornylidenemethyl)benzene and salts thereof and 2,4-bis{[4-(2-ethylhexyloxy)-2-hydroxy]phenyl}-6-(4-methoxyphenyl)-1,3,5-triazine, in each case individually or in any combinations with one another.

The water-soluble substances are advantageously:

2-phenylbenzimidazole-5-sulfonic acid, phenylene-1,4-bis(2-benzimidazyl)3,3'-5,5'-tetrasulfonic acid and salts thereof, e.g. sodium, potassium or triethanolammonium salts, and the sulfonic acid itself;

sulfonic acid derivatives of benzophenones, preferably 2-hydroxy-4-methoxybenzophenone-5-sulfonic acid and its salts; and sulfonic acid derivatives of 3-benzylidenecamphor, such as, for example, 4-(2-oxo-3-bornylidenemethyl)benzenesulfonic acid, 2-methyl-5-(2-oxo-3-bornylidenemethyl)sulfonic acid and its salts.

A further photoprotective filter substance to be used advantageously according to the invention is ethylhexyl 2-cyano-3,3-diphenylacrylate (octocrylene), which is available from BASF under the name Uvinul® N 539. It may also be of considerable advantage to use polymer-bound or polymeric UV filter substances in preparations according to the present invention, in particular those as are described in WO-A-92/20690.

In addition, it may in some instances be advantageous to incorporate, in accordance with the invention, further UV-A or UV-B filters into cosmetic or dermatological preparations, for example certain salicylic acid derivatives, such as 4-isopropylbenzyl salicylate, 2-ethylhexyl salicylate (=octyl salicylate), homomenthyl salicylate. The list of UVB filters mentioned which can be used according to the invention is not of course intended to be limiting.

The invention also provides the combination of a UVA filter according to the invention with a UVB filter or a cosmetic or dermatological preparation according to the invention which also comprises a UVB filter.

It may also be advantageous to incorporate UVA filters that are usually present in cosmetic or dermatological preparations into preparations according to the invention. Such substances are preferably derivatives of dibenzoylmethane, in particular 1-(4'-tert-butylphenyl)-3-(4'-methoxyphenyl)propane-1,3-dione and 1-phenyl-3-(4'-isopropylphenyl)propane-1,3-dione. Preparations which comprise these combinations are also provided by the invention. It is possible to use the same amounts of UVA filter substances which have been specified for UVB filter substances.

Cosmetic or dermatological preparations according to the invention may also comprise inorganic pigments which are customarily used in cosmetics for protecting the skin against UV rays. These are oxides of titanium, zinc, iron, zirconium, silicon, manganese, aluminum, cerium and mixtures thereof, and also modifications in which the oxides are the active agents. They are particularly preferably pigments based on titanium dioxide. The amounts specified for the abovementioned combinations may be used.

A surprising property of the present invention is that preparations according to the invention are very good vehicles for cosmetic or dermatological active ingredients into the skin, advantageous active ingredients being antioxidants which can protect the skin against oxidative stress.

According to the invention, the preparations advantageously comprise one or more antioxidants. Favorable, but nevertheless optional, antioxidants to be used are all antioxidants which are customary or suitable for cosmetic or dermatological applications. In this connection, it is advantageous to use antioxidants as the sole class of active ingredient when, for example, a cosmetic or dermatological application is at the forefront, such as controlling the oxidative stress of the skin. It is, however, also favorable to provide the preparations according to the invention with a content Of one or more antioxidants if the preparations are to serve another purpose, e.g. as deodorants or sunscreens.

The antioxidants are advantageously chosen from the group consisting of amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotenoids, carotenes (e.g. α-carotene, β-carotene, lycopene) and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof), and also salts thereof, dilauryl thiodipropionate, distearyl thiodipropionate, thiodipropionic acid and derivatives thereof (esters, ethers, peptides, lipids, nucleotides, nucleosides and salts), and also sulfoximine compounds (e.g. buthionine sulfoximines, homocysteine sulfoximine, buthionine sulfones, penta-, hexa-, heptathionine sulfoximine) in very low tolerated doses (e.g. pmol to μmol/kg), and also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate), and coniferyl benzoate of benzoin resin, rutinic acid and derivatives thereof, ferulic acid and derivatives thereof, butylhydroxytoluene, butylhydroxyanisole, nordihydroguaiacic acid, nordihydroguaiaretic acid, trihydroxybutyrophenone, uric acid and derivatives thereof, mannose and derivatives thereof, zinc and derivatives thereof (e.g. ZnO, $ZnSO_4$), selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids) of these said active ingredients which are suitable according to the invention. For the purposes of the present invention, water-soluble antioxidants may be used particularly advantageously.

A surprising property of the preparations according to the invention is that they are very good vehicles for cosmetic or dermatological active ingredients into the skin, preferred active ingredients being antioxidants which can protect the skin against oxidative stress. Preferred antioxidants here are vitamin E and derivatives thereof, and vitamin A and derivatives thereof.

The amount of antioxidants (one or more compounds) in the preparations is preferably 0.001 to 30% by weight, particularly preferably 0.05 to 20% by weight, in particular 0.1 to 10% by weight, based on the total weight of the preparation.

If vitamin E and derivatives thereof are the antioxidant or the antioxidants, it is advantageous to choose their particular concentrations from the range from 0.001 to 10% by weight, based on the total weight of the formulation.

If vitamin A or vitamin A derivatives, or carotenes or derivatives thereof are the antioxidant or the antioxidants, it is advantageous to choose their particular concentrations from the range from 0.001 to 10% by weight, based on the total weight of the formulation.

According to the invention, the active ingredients (one or more compounds) can also very advantageously be chosen from the group of lipophilic active ingredients, in particular from the following group: acetylsalicylic acid, atropine, azulene, hydrocortisone and derivatives thereof, e.g. hydrocortisone-17 valerate, vitamins, e.g. ascorbic acid and derivatives thereof, vitamins of the B and D series, very favorably vitamin $B_1$, vitamin $B_{12}$, vitamin $D_1$, but also bisabolol, unsaturated fatty acids, namely the essential fatty acids (often also called vitamin F), in particular gamma-linolenic acid, oleic acid, eicosapentanoic acid, docosahexanoic acid and derivatives thereof, chloramphenicol, caffeine, prostaglandins, thymol, camphor, extracts or other products of a vegetable and animal origin, e.g. evening primrose oil, borage oil or currant seed oil, fish oils, cod-liver oil and also ceramides and ceramide-like compounds, etc.

It is also advantageous to choose the active ingredients from the group of refatting substances, for example purcellin oil, Eucerit® and Neocerit®.

The active ingredient or ingredients are particularly advantageously chosen from the group of NO synthase inhibitors, particularly if the preparations according to the invention are to be used for the treatment and prophylaxis of the symptoms of intrinsic and extrinsic skin aging and for the treatment and prophylaxis of the harmful effects of ultraviolet radiation on the skin. A preferred NO synthase inhibitor is nitroarginine.

The active ingredient or ingredients are further advantageously chosen from the group which includes catechins and bile esters of catechins and aqueous or organic extracts from plants or parts of plants which have a content of catechins or bile esters of catechins, such as, for example, the leaves of the theaceae plant family, in particular of the species Camellia sinensis (green tea). Their typical ingredients (such as, for example, polyphenols or catechins, caffeine, vitamins, sugars, minerals, amino acids, lipids) are particularly advantageous. Catechins are a group of compounds which are to be regarded as hydrogenated flavones or anthocyanidins and are derivatives of "catechin" (catechol, 3,3',4',5,7-flavanpentol, 2-(3,4-dihydroxyphenyl)chroman-3,5,7-triol). Epicatechin ((2R,3R)-3,3',4',5,7-flavanpentol) is also an advantageous active ingredient for the purposes of the present invention.

Also advantageous are plant extracts with a content of catechins, in particular extracts of green tea, such as, for example, extracts from leaves of the plants of the species *Camellia* spec., very particularly of the tea types *Camellia sinensis, C. assamica, C. taliensis* and *C. irrawadiensis* and hybrids of these with, for example, *Camellia japonica*.

Preferred active ingredients are also polyphenols and catechins from the group consisting of (−)-catechin, (+)-catechin, (−)-catechin gallate, (−)-gallocatechin gallate, (+)-epicatechin, (−)-epicatechin, (−)-epicatechin gallate, (−)-epigallocatechin, (−)-epigallocatechin gallate.

Flavone and its derivatives (also often collectively called "lavones") are also advantageous active ingredients for the purposes of the present invention. They are characterized by the following basic structure (substitution positions are shown):

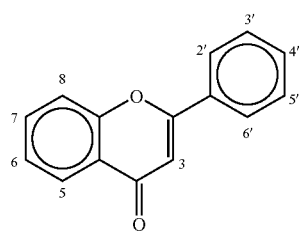

Some of the more important flavones which can also preferably be used in preparations according to the invention are given in the table below:

|  | OH substitution positions | | | | | | | |
| --- | --- | --- | --- | --- | --- | --- | --- | --- |
|  | 3 | 5 | 7 | 8 | 2' | 3' | 4' | 5' |
| Flavone | − | − | − | − | − | − | − | − |
| Flavonol | + | − | − | − | − | − | − | − |
| Chrysin | − | + | + | − | − | − | − | − |
| Galangin | + | + | + | − | − | − | − | − |
| Apigenin | − | + | + | − | − | − | + | − |
| Fisetin | + | − | + | − | − | + | + | − |
| Luteolin | − | + | + | − | − | + | + | − |
| Kaempferol | + | + | + | − | − | − | + | − |
| Quercetin | + | + | + | − | − | + | + | − |
| Morin | + | + | + | − | + | − | + | − |
| Robinetin | + | − | + | − | − | + | + | + |
| Gossypetin | + | + | + | + | − | + | + | − |
| Myricetin | + | + | + | − | − | + | + | + |

In nature, flavones are usually in glycosylated form. According to the invention, the flavonoids are preferably chosen from the group of substances of the generic structural formula:

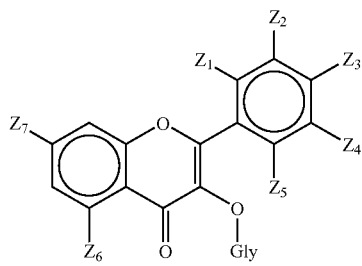

where $Z_1$ to $Z_7$, independently of one another, are chosen from the group consisting of H, OH, alkoxy and hydroxyalkoxy groups, where the alkoxy and hydroxyalkoxy groups can be branched or unbranched and may have 1 to 18 carbon atoms, and where Gly is chosen from the group of mono- and oligoglycoside radicals.

According to the invention, the flavonoids can, however, also be chosen advantageously from the group of substances of the generic structural formula:

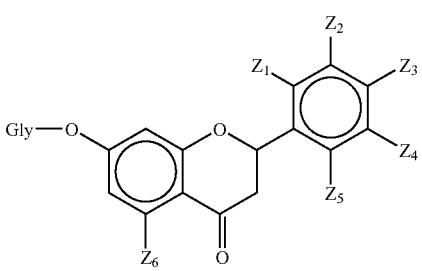

where $Z_1$ to $Z_6$, independently of one another, are chosen from the group consisting of H, OH, alkoxy and hydroxyalkoxy groups, where the alkoxy and hydroxyalkoxy groups may be branched or unbranched and have 1 to 18 carbon atoms, and where Gly is chosen from the group of mono- and oligoglycoside radicals.

Preferably, such structures can be chosen from the group of substances of the generic structural formula:

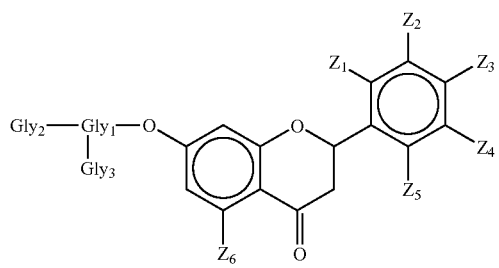

where $Gly_1$, $Gly_2$ and $Gly_3$, independently of one another, are monoglycoside radicals or. $Gly_2$ and $Gly_3$ may also, individually or together, represent saturations by hydrogen atoms.

Preferably, $Gly_1$, $Gly_2$ and $Gly_3$, independently of one another, are chosen from the group of hexosyl radicals, in particular the rhamnosyl radicals and glucosyl radicals. However, other hexosyl radicals, for example allosyl, altrosyl, galactosyl, gulosyl, idosyl, mannosyl and talosyl, can also be used advantageously in some circumstances. It may also be advantageous according to the invention to use pentosyl radicals.

Advantageously, $Z_1$ to $Z_5$, independently of one another, are chosen from the group consisting of H, OH, methoxy, ethoxy and 2-hydroxyethoxy, and the flavone glycosides have the structure:

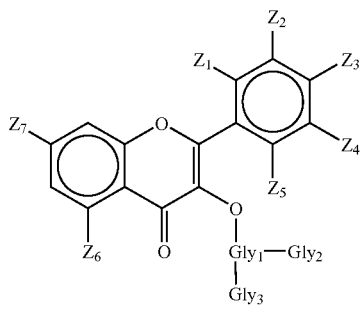

The flavone glycosides according to the invention are particularly advantageously from the group given by the following structure:

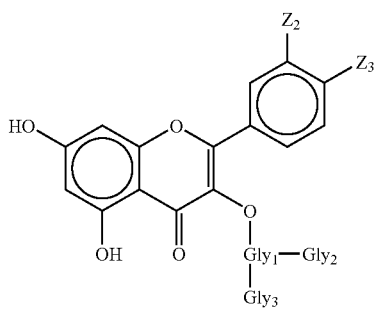

where $Gly_1$, $Gly_2$ and $Gly_3$, independently of one another, are monoglycoside radicals or. $Gly_2$ and $Gly_3$ may also, individually or together, represent saturations by hydrogen atoms.

Preferably, $Gly_1$, $Gly_2$ and $Gly_3$ are chosen independently of one another from the group of hexosyl radicals, in particular the rhamnosyl radicals and glucosyl radicals. However, other hexosyl radicals, for example allosyl, altrosyl, galactosyl, gulosyl, idosyl, mannosyl and talosyl, can also advantageously be used in some circumstances. It may also be advantageous according to the invention to use pentosyl radicals.

For the purposes of the present invention, it is particularly advantageous to choose the flavone glycoside(s) from the group consisting of α-glucosylrutin, α-glucosylmyricetin, α-glucosylisoquercitrin, α-glucosylisoquercetin and α-glucosylquercitrin. According to the invention, particular preference is given to α-glucosylrutin.

Also advantageous according to the invention are naringin (aurantin, naringenin-7-rhamnoglucoside), hesperidin (3',5, 7-trihydroxy-4'-methoxyflavanone-7-rutinoside, hesperidoside, hesperetin-7-O-rutinoside), rutin (3,3',4',5,7-pentahydroxyflyvon-3-rutinoside, quercetin-3-rutinoside, sophorin, birutan, rutabion, taururtin, phytomelin, melin), troxerutin (3,5-dihydroxy-3',4',7-tris(2-hydroxyethoxy)flavone-3-(6-O-(6-deoxy-α-L-mannopyranosyl)-β-D-glucopyranoside)), monoxerutin (3,3',4',5-tetrahydroxy-7-(2-hydroxyethoxy) flavone-3-(6-O-(6-deoxy-α-L-mannopyranosyl)-β-D-glucopyranoside)), dihydrorobinetin (3,3',4',5',7-pentahydroxyflavanone), taxifolin (3,3',4',5,7-pentahydroxyflavanone), eriodictyol-7-glucoside (3',4',5,7-tetrahydroxyflavanone-7-glucoside), flavanomarein (3',4',7,8-tetrahydroxyflavanone-7-glucoside) and isoquercetin (3,3',4',5,7-pentahydroxyflavanone-3-(β-D-glucopyranoside).

It is also advantageous to choose the active ingredient(s) from the group of ubiquinones and plastoquinones. Ubiquinones are characterized by the structural formula:

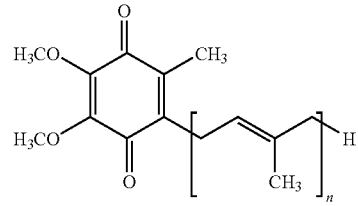

and are the most widespread and thus the most investigated bioquinones. Ubiquinones are referred to, depending on the number of isoprene units linked in the side chain, as Q-1, Q-2, Q-3 etc., or, according to the number of carbon atoms, as U-5, U-10, U-15 etc. They preferably arise with certain chain lengths, e.g. in some microorganisms and yeasts where n=6. In most mammals including man, Q10 predominates.

Coenzyme Q10 is particularly advantageous and is characterized by the following structural formula:

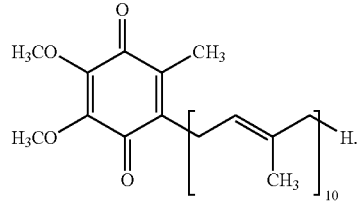

Plastoquinones have the general structural formula:

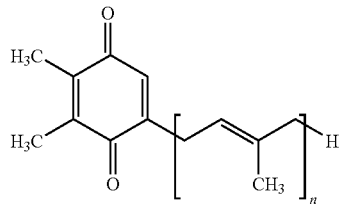

Plastoquinones differ in the number n of isoprene radicals and are referred to accordingly, e.g. PQ-9 (n=9). In addition, other plastoquinones with varying substituents on the quinone ring exist.

Creatine and creatinee derivatives, phosphocreatinee are also preferred active ingredients for the purposes of the present invention. Creatine is characterized by the following structure:

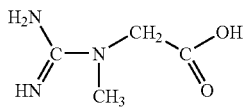

Preferred derivatives are creatinee phosphate, and creatinee sulfate, creatinee acetate, creatinee ascorbate and the derivatives esterified on the carboxyl group with mono- or polyfunctional alcohols.

A further advantageous active ingredient is L-carnitine [3-hydroxy-4-(trimethyl-ammonio)butyrobetaine]. Acylcarnitines, chosen from the group of substances of the following general structural formula:

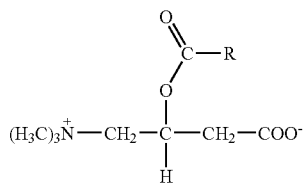

where R is chosen from the group of branched and unbranched alkyl radicals having up to 10 carbon atoms, are also advantageous active ingredients for the purposes of the present invention. Preference is given to propionylcarnitine and, in particular, acetylcarnitine. Both enantiomers (D and L form) are to be used advantageously for the purposes of the present invention. It may also be advantageous to use any enantiomer mixtures, for example a racemate of D and L form.

Further advantageous active ingredients are sericoside, pyridoxol, aminoguadine, phytochelatin, isoflavones (genistein, daidzein, daidzin, glycitin), niacin, tyrosine sulfate, dioic acid, adenosine, pyridoxine, arginine, vitamin K, biotin and aroma substances.

The list of said active ingredients and active ingredient combinations which can be used in the preparations according to the invention is not of course intended to be limiting. The active ingredients can be used individually or in any combinations with one another.

Active ingredients may be present in the preparations in the amounts of 0.0001 to 25% by weight, preferably 0.001 to 20% by weight, in particular 0.01 to 10% by weight, in each case based on the total weight of the preparations.

Although the use of hydrophilic active ingredients is of course also favored according to the invention, a further advantage of the preparations according to the invention is that the high number of very finely divided droplets makes oil-soluble and lipophilic active ingredients in particular bioavailable with particularly good effectiveness.

It is also advantageous to choose the active ingredients from the group of refatting substances, for example purcellin oil, Eucerit® and Neocerit®.

It is also possible and in some instances advantageous to add washing-active surfactants to the preparations according to the invention. Aqueous cosmetic cleansing agents according to the invention or low-water or anhydrous cleansing agent concentrates intended for aqueous cleansing can comprise cationic, anionic, nonionic or amphoteric surfactants, for example conventional soaps, e.g. fatty acid salts of sodium, alkyl sulfates, alkyl ether sulfates, alkane- and alkylbenzenesulfonates, sulfoacetates, sulfobetaines, sarcosinates, amidosulfobetaines, sulfosuccinates, sulfosuccinic monoesters, alkyl ether carboxylates, protein-fatty acid condensates, alkylbetaines and amidobetaines, fatty acid alkanolamides, polyglycol ether derivatives.

Cosmetic preparations which are cosmetic cleansing preparations for the skin may be present in liquid or semisolid form, for example in the form of gels. They preferably comprise at least one anionic, cationic, nonionic or amphoteric surface-active substance or mixtures thereof, optionally electrolytes and auxiliaries, as are customarily used for this purpose. The surface-active substance can preferably be present in a concentration between 1 and 30% by weight in the cleansing preparations, based on the total weight of the preparations.

Cosmetic preparations which are shampoos preferably comprise at least one anionic, nonionic or amphoteric surface-active substance or mixtures thereof, optionally electrolytes and auxiliaries as are customarily used for this purpose. The surface-active substance can preferably be present in a concentration between 1 and 50% by weight in the cleansing preparations, based on the total weight of the preparations. Cetyltrimethylammonium salts, for example, are to be used advantageously.

The preparations according to the invention intended for the cleansing of hair or skin comprise, apart from the above-mentioned surfactants, water and optionally the additives customary in cosmetics, for example perfume, thickeners, dyes, deodorants, antimicrobial substances, refatting agents, complexing agents and sequestrants, pearlescence agents, plant extracts, vitamins, active ingredients and the like.

Despite their oil content, the preparations according to the invention surprisingly have very good foam development, high cleansing power and have a high regenerating effect with regard to the general condition of the skin. In particular, the preparations according to the invention have a skin-smoothing effect, reduce the feeling of dryness of the skin and make the skin supple.

If the preparations according to the invention are to be used for hair care, they can comprise the customary constituents, usually, for example, film-forming polymers. Of such polymers with at least partially quaternized nitrogen groups (called below "film formers"), those which are chosen from the group of substances which carry the name "Polyquaternium" according to INCI nomenclature (International Nomenclature Cosmetic Ingredient) are preferably suitable, for example:

Polyquaternium-2 (Chemical Abstracts No.63451-27-4, e.g. Mirapol® A-15);

Polyquaternium-5 (copolymer of acrylamide and β-methacryloxyethyltrimethyl-ammonium methosulfate, CAS No. 26006-22-4);

Polyquaternium-6 (homopolymer of N,N-dimethyl-N-2-propenyl-2-propen-1-aminium chloride, CAS No. 26062-79-3, e.g. Merquat® 100);

Polyquaternium-7 N,N-dimethyl-N-2-propenyl-2-propen-1-aminium chloride, polymer with 2-propenamide, CAS No. 26590-05-6, e.g. Merquat® S;

Polyquaternium-10 quaternary ammonium salt of hydroxyethylcellulose, CAS No. 53568-66-4, 55353-19-0, 54351-50-7, 68610-92-4, 81859-24-7, e.g. Celquat® SC-230M;

Polyquaternium-11 vinylpyrrolidone/dimethylaminoethyl methacrylate copolymer/diethyl sulfate reaction product, CAS No. 53633-54-8, e.g. Gafquat® 755N;

Polyquaternium-16 vinylpyrrolidone/vinylimidazolinium methochloride copolymer, CAS No. 29297-55-0, e.g. Luviquat® HM 552;

Polyquaternium-17 CAS No. 90624-75-2, e.g. Mirapol® AD-1;

Polyquaternium-19 quaternized water-soluble polyvinyl alcohol;

Polyquaternium-20 water-dispersible quaternized polyvinyl octadecyl ether;

Polyquaternium-21 polysiloxane-polydimethyl-dimethylammonium acetate; copolymer, e.g. Abil® B 9905;

Polyquaternium-22 dimethyldiallylammonium chloride/acrylic acid copolymer, CAS No. 53694-7-0, e.g. Merquat® 280;

Polyquaternium-24 polymeric quaternary ammonium salt of hydroxyethylcellulose, reaction product with an epoxide substituted by lauryldimethylammonium, CAS No. 107987-23-5, e.g. Quatrisoft® LM-200;

Polyquaternium-28 vinylpyrrolidone/methacrylamidopropyltrimethylammonium chloride copolymer, e.g. Gafquat® HS-100;

Polyquaternium-29 e.g. Lexquat® CH;

Polyquaternium-31 CAS No. 136505-02-7, e.g. Hypane QT 100;

Polyquaternium-32 N,N,N-trimethyl-2-[(2-methyl-1-oxo-2-propenyl)oxy]ethanaminium chloride, polymer with 2-propenamide, CAS No. 35429-19-7;

Polyquaternium-37 CAS No. 26161-33-1;

Cetyltrimethylammonium salts such as CTAB, CTAC.

Hair care preparations according to the invention advantageously comprise 0.01 to 5% by weight of one or more film formers, preferably 0.1 to 3% by weight, in particular 0.2 to 2% by weight, in each case based on the total weight of the preparations. Such embodiments of the preparations according to the invention care for hair which has been stripped or damaged by environmental influences, or protect against such influences. In addition, the preparations according to the invention give the hairstyle relaxed fullness and strength without having a sticky effect.

Correspondingly, depending on their formulation, the preparations according to the invention can, for example, be used as skin protection emulsion, cleansing milk, sunscreen lotion, nutrient lotion, day or night emulsion etc.

The preparations according to the invention further advantageously contribute to skin smoothing, particularly when they are provided with one or more substances which promote skin smoothing.

It is in some cases possible and advantageous to use the preparations according to the invention as bases for pharmaceutical formulations. Corresponding requirements apply mutatis mutandis to the formulation of medicinal preparations. The boundaries between pure cosmetics and pure pharmaceuticals are fluid here. According to the invention, suitable pharmaceutical active ingredients are fundamentally all classes of active ingredient, preference being given to lipophilic active ingredients. Examples are: antihistamines, antiphlogistics, antibiotics, antimycotics, active ingredients which promote circulation, keratolytics, hormones, steroids, vitamins etc.

The cosmetic and dermatological preparations according to the invention can comprise cosmetic auxiliaries as are customarily used in such preparations, e.g. preservatives, bactericides, virucides, perfumes, substances for preventing foaming, dyes, pigments which have a coloring effect, thickeners, surface-active substances, emulsifiers, softening, moisturizing and humectant substances, anti-inflammatory substances, medicaments, fats, oils, waxes or other customary constituents of a cosmetic or dermatological formulation, such as alcohols, polyols, polymers, foam stabilizers, electrolytes, organic solvents. Mixtures of the abovementioned solvents are used particularly advantageously.

Further constituents which may be used are fats, waxes and other natural and synthetic fatty bodies, preferably esters of fatty acids with alcohols of low carbon number, e.g. with isopropanol, propylene glycol or glycerol, or esters of fatty alcohols with alkanoic acids of low carbon number or with fatty acids, alcohols, diols or polyols of low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products.

Unless stated otherwise, all amounts, percentages or parts refer to the weight of the preparations or of the particular mixture.

EXAMPLES

The examples below are intended to illustrate the present invention.

Example 1

|  | % by wt. |
| --- | --- |
| Isoceteth-20 | 1.700 |
| Glyceryl stearate | 5.300 |
| Coco caprylate caprate | 5.000 |
| Dicaprylyl ether | 5.000 |
| PEG-150 distearate | 0.800 |
| Glycerol | 3.000 |
| Water | ad 100.000 |

Example 2

|  | % by wt. |
| --- | --- |
| Isoceteth-20 | 4.600 |
| Glyceryl stearate | 2.400 |
| Dicapryl ether | 5.000 |
| Cyclomethicone | 5.000 |
| PEG-150 distearate | 1.000 |
| Glycerol | 3.000 |
| Water | ad 100.000 |

Example 3

|  | % by wt. |
| --- | --- |
| Isoceteth-20 | 4.600 |
| Sorbitan isostearate | 2.400 |
| Dicapryl ether | 5.000 |
| Cyclomethicone | 5.000 |
| Coco caprylate caprate | 5.000 |
| PEG-150 distearate | 1.000 |
| Glycerol | 3.000 |
| Water | ad 100.000 |

Example 4

| | % by wt. |
|---|---|
| PEG-20 sorbitan isostearate | 4.600 |
| Sorbitan isostearate | 2.400 |
| Diethylhexylcyclohexane | 5.000 |
| PEG-150 distearate | 1.000 |
| Glycerol | 2.000 |
| Water | ad 100.000 |

Example 5

| | % by wt. |
|---|---|
| PEG-25 stearate | 4.600 |
| Glyceryl stearate | 2.400 |
| Dicapryl ether | 5.000 |
| Octyldodecanol | 5.000 |
| PEG-150 distearate | 0.800 |
| Glycerol | 3.000 |
| Water | ad 100.000 |

Example 6

| | % by wt. |
|---|---|
| PEG-25 stearate | 4.600 |
| Glyceryl stearate | 2.400 |
| Dicapryl ether | 5.000 |
| Paraffinum Liquidum | 5.000 |
| PEG-150 distearate | 0.800 |
| Glycerol | 3.000 |
| Water | ad 100.000 |

Example 7

| | % by wt. |
|---|---|
| Ceteareth-20 | 1.000 |
| Caprylic/capric triglyceride | 1.000 |
| Cetearyl isononanoate | 3.000 |
| C12-15 alkyl benzoate | 3.000 |
| PEG-150 distearate | 2.000 |
| Dimethicone | 3.000 |
| Glycerol | 3.000 |
| Water | ad 100.000 |

Example 8

| | % by wt. |
|---|---|
| Sorbitan stearate | 1.000 |
| Polyglyceryl-3 methylglucose distearate | 3.000 |
| C12-15 alkyl benzoate | 4.000 |
| Cetearyl alcohol | 1.500 |
| PEG-150 distearate | 1.000 |
| Cyclomethicone | 3.000 |
| Glycerol | 5.000 |
| Water | ad 100.000 |

Example 9

| | % by wt. |
|---|---|
| Glyceryl stearate | 1.500 |
| Ceteareth-20 | 2.000 |
| Myristyl myristate | 4.000 |
| Isostearyl isostearate | 5.000 |
| C12-15 alkyl benzoate | 5.000 |
| Squalane | 1.000 |
| Behenyl alcohol | 2.500 |
| Dimethicone | 2.000 |
| PEG-150 distearate | 1.000 |
| Butylene glycol | 5.000 |
| Water | ad 100.000 |

Example 10

| | % by wt. |
|---|---|
| Polyglyceryl-3 methylglucose distearate | 5.000 |
| Cetyl alcohol | 1.500 |
| Paraffinum Liquidum | 3.000 |
| Dimethicone | 2.000 |
| Isostearyl isostearate | 4.000 |
| Cyclomethicone | 4.000 |
| Butylene glycol | 5.000 |
| Water | ad 100.000 |

Example 11

| | % by wt. |
|---|---|
| Sorbitan stearate | 1.000 |
| Polyglyceryl-3 methylglucose distearate | 3.000 |
| C12-15 alkyl benzoate | 4.000 |
| Cetearyl alcohol | 0.500 |
| PEG-150 distearate | 1.500 |
| Cyclomethicone | 3.000 |
| Glycerol | 5.000 |
| Water | ad 100.000 |

Example 12

| | % by wt. |
|---|---|
| Sorbitan stearate | 1.000 |
| Polyglyceryl-3 methylglucose distearate | 3.000 |

-continued

|  | % by wt. |
| --- | --- |
| C12-15 alkyl benzoate | 4.000 |
| PEG-150 distearate | 2.000 |
| Cyclomethicone | 3.000 |
| Glycerol | 5.000 |
| Water | ad 100.000 |

Example 13

|  | % by wt. |
| --- | --- |
| Ceteareth-20 | 1.000 |
| Caprylic/capric triglyceride | 1.000 |
| Cetearyl isononanoate | 3.000 |
| C12-15 alkyl benzoate | 3.000 |
| PEG-150 distearate | 2.000 |
| Dimethicone | 3.000 |
| Glycerol | 3.000 |
| Water | ad 100.000 |

That which is claimed:

1. A crosslinked oil-in water emulsion, wherein the emulsion comprises:
   a continuous aqueous phase;
   a discontinuous oil phase comprising droplets having a diameter of from about 50 μm to about 200 μm;
   one or more oil-in-water emulsifiers; and
   one or more crosslinker substances which are capable of joining at least a portion of the emulsion droplets together, wherein molecules of the crosslinker substances comprise at least one hydrophilic region comprising an expansion that bridges the distance between at least two emulsion droplets and at least one hydrophobic region that forms a hydrophobic interaction with at least one of the emulsion droplets, the one or more crosslinker substances being present in a concentration of from 0.001% to 20% by weight, based on a total weight of the emulsion.

2. The emulsion of claim 1, wherein the one or more crosslinker substances are present in a concentration of from 0.1% to 5% by weight.

3. The emulsion of claim 1, wherein the one or more crosslinker substances comprise one or more substances of the following formulae:

A—B—A   (1)

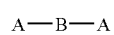   (2)

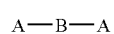   (3)

   (4)

A—B—A—B—A   (5)

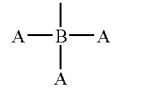

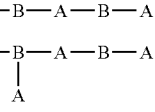

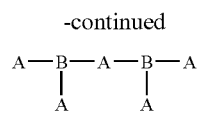   (6)

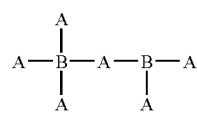   (7)

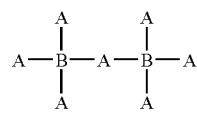   (8)

A—B—Z—B—A   (9)

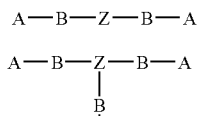   (10)

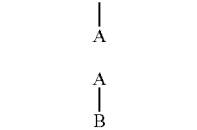   (11)

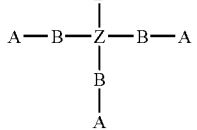   (12)

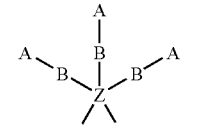

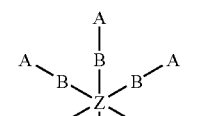   (13)

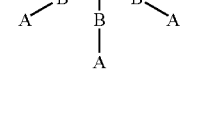

wherein:
   A is a hydrophobic region;
   B is a hydrophilic region; and
   Z is a central unit which is hydrophilic or hydrophobic.

4. The emulsion of claim 1, wherein the at least one hydrophilic region comprises a structure of formula:

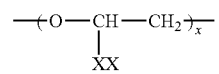

wherein:
   x is a number of from 20 to 300; and
   xx is H, $CH_3$, or OH.

5. The emulsion of claim 1, wherein the one or more crosslinker substances comprise one or more substances of the following formulae:

R₁—(O—CH₂—CH₂)ₓ—O—R₂

R₁—O—(CH₂—CH—CH₂—O)ₓ—R₂
            |
            OH

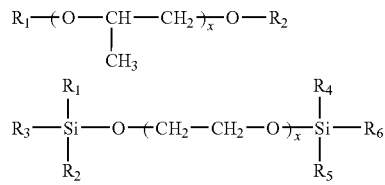

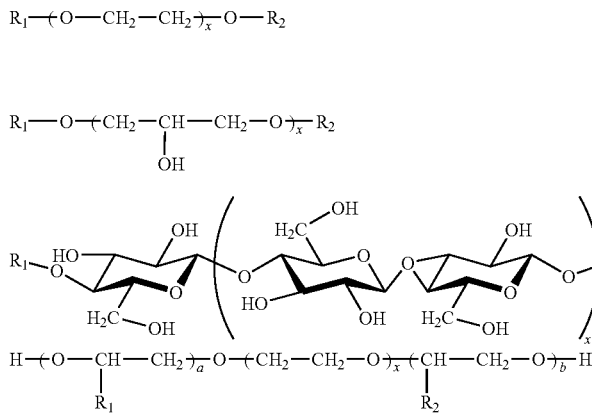

H—(O—CH—CH₂)ₐ—O—(CH₂—CH₂—O)ₓ—(CH—CH₂—O)ᵦ—H
         |                          |
         R₁                         R₂ wherein $R_1$ to $R_6$, independently of one another, represent branched or unbranched, saturated or unsaturated, cyclic or chain-like aliphatic, aromatic or heteroaromatic radicals, x is from 20 to 300 and a and b are numbers which allow the molecule to be soluble or dispersible in water.

6. The emulsion of claim 1, wherein the one or more crosslinker substances comprise one or more of PEG-150 distearate, PEG-800 distearate, PEG-800 chol₂, PEG-150 dioleate, PEG-300 pentaerythrityl tetraisostearate, PEG-120 methyl glucose dioleate, PEG-160 sorbitan triisostearate, PEG-450 sorbitol hexaisostearate, PEG-230 glyceryl triisostearate, PEG-200 glyceryl palmitate, polyether-1, one or more of polyurethane crosslinkers Rheolate 204, 205, 208, and cetylhydroxyethylcellulose.

7. The emulsion of claim 1, wherein the one or more crosslinker substances comprise PEG-150 distearate.

8. The emulsion of claim 1, wherein the one or more crosslinker substances comprise one or more substances selected from hydrophobically substituted cellulose ethers, starches, acrylates, alginates, glucans, chitins, dextrans, caseinates, pectins, proteins and gums, polyurethanes, polyacrylamides, polyvinyl alcohols, polyacrylates, and water-soluble silicone polymers.

9. The emulsion of claim 1, wherein the one or more oil-in-water emulsifiers comprise one or more of ceteth-15, ceteth-16, ceteareth-15, ceteareth-16, ceteareth-20, isoceteth-20, isosteareth-20, steareth-20, oleth-15, laureth-15, PEG-20 stearate, PEG-25 stearate, PEG-20 oleate, PEG-20 sorbitan stearate, PEG-20 sorbitan isostearate, PEG-20 sorbitan oleate, sodium laureth-11carboxylate, sodium lauryl ether sulfate, PEG-30 cholesteryl ether, PEG-60 evening primrose glyceride, bis PEG/PPG-16/16 PEG/PPG16/16 dimethicone+caprylic/capric triglyceride, PEG-45palm kernel oil glyceride, PEG-20 glyceryl laurate, PEG-20 glyceryl stearate, and PEG-20 glycerol isostearate.

10. The emulsion of claim 1, wherein the one or more oil-in-water emulsifiers comprise isoceteth-20.

11. The emulsion of claim 1, wherein the emulsion further comprises one or more water-in-oil emulsifiers.

12. The emulsion of claim 11, wherein the one or more water-in-oil emulsifiers comprise one or more substances selected from glyceryl stearate, glycerol isostearate, glyceryl linoleate, diglycerol isostearate, triglycerol diisostearate, sorbitan isostearate, propylene glycol isostearate, propylene glycol stearate, cetyl alcohol, stearyl alcohol, steareth-2, glyceryl laurate, glyceryl caprinate, glyceryl caprylate, selachyl alcohol, chimyl alcohol, PEG-5 cholesteryl ether PEG-30 dipolyhydroxystearate, polyglyceryl-3 methylglucose distearate, PEG-45/dodecyl glycol copolymer, methoxy-PEG-22-dodecyl glycol copolymer, methylglucose sesquistearate, polyglyceryl-2 dipolyhydroxystearate, cetyl dimethicone copolyols, alkyl methicone copolyols, and alkyl dimethicone ethoxy glucosides.

13. The emulsion of claim 12, wherein the one or more water-in-oil emulsifiers comprise polyglyceryl-3 methylglucose distearate.

14. The emulsion of claim 1, wherein the one or more crosslinker substances comprise one or more water-soluble substances.

15. The emulsion of claim 1, wherein the emulsion further comprises at least one active ingredient selected from one or more of antioxidants, UV filters, refatting substances, antiperspirant substances, perfumes, electrolytes, and skin moisturizing agents.

16. The emulsion of claim 15, wherein the at least one active ingredient comprises an antioxidant.

17. The emulsion of claim 15, wherein the at least one active ingredient is present in a concentration of from 0.01% to 10% by weight, based on a total weight of the emulsion.

18. The emulsion of claim 1, wherein the emulsion is present in liquid form.

19. The emulsion of claim 1, wherein the emulsion is present as a cream or a lotion.

20. The emulsion of claim 1, wherein the emulsion is present as a gel.

21. The emulsion of claim 1, wherein the emulsion is present as a face cleansing product.

22. The emulsion of claim 1, wherein the emulsion is present as a shampoo.

23. The emulsion of claim 1, wherein the emulsion further comprises one or more surfactants.

24. A crosslinked oil-in water emulsion, wherein the emulsion comprises:
a continuous aqueous phase;
a discontinuous oil phase comprising droplets having a diameter of from about 50 μm to about 200 μm;
one or more oil-in-water emulsifiers comprising one or more of ceteth-15, ceteth-16, ceteareth-15, ceteareth-16, ceteareth-20, isoceteth-20, isosteareth-20, steareth-20, oleth-15, laureth-15, PEG-20 stearate, PEG-25 stearate, PEG-20 oleate, PEG-20 sorbitan stearate, PEG-20 sorbitan isostearate, PEG-20 sorbitan oleate, sodium laureth-11 carboxylate, sodium lauryl ether sulfate, PEG-30 cholesteryl ether, PEG-60 evening primrose glyceride, his PEG/PPG-16/16 PEG/PPG16/16 dimethicone+caprylic/capric triglyceride, PEG-45 palm kernel oil glyceride, PEG-20 glyceryl laurate, PEG-20 glyceryl stearate, and PEG-20 glycerol isostearate; and one or more crosslinker substances comprising one or more of PEG-150 distearate, PEG-800 distearate, PEG-800 chol$_2$, PEG-150 dioleate, PEG-300 pentaerythrityl tetraisostearate, PEG-120 methyl glucose dioleate, PEG-160 sorbitan triisostearate, PEG-450 sorbitol hexaisostearate, PEG-230 glyceryl triisostearate, PEG-200 glyceryl palmitate, polyether-1, one or more of polyurethane crosslinkers Rheolate 204, 205, 208, and cetylhydroxyethylcellulose, the one or more crosslinker substances being present in a concentration of from 0.1% to 5% by weight, based on a total weight of the emulsion.

25. The emulsion of claim 24, wherein the one or more crosslinker substances comprise PEG-150 distearate.

26. The emulsion of claim 25 wherein the one or more oil-in-water emulsifiers comprise isoceteth-20.

27. The emulsion of claim 24, wherein the emulsion further comprises one or more water-in-oil emulsifiers.

28. The emulsion of claim 27, wherein the one or more water-in-oil emulsifiers comprise one or more substances selected from glyceryl stearate, glycerol isostearate, glyceryl linoleate, diglycerol isostearate, triglycerol diisostearate, sorbitan isostearate, propylene glycol isostearate, propylene glycol stearate, cetyl alcohol, stearyl alcohol, steareth-2, glyceryl laurate, glyceryl caprinate, glyceryl caprylate, selachyl alcohol, chimyl alcohol, PEG-5 cholesteryl ether PEG-30 dipolyhydroxystearate, polyglyceryl-3 methylglucose distearate, PEG-45/dodecyl glycol copolymer, methoxy-PEG-22-dodecyl glycol copolymer, methylglucose sesquistearate, polyglyceryl-2 dipolyhydroxystearate, cetyl dimethicone copolyols, alkyl methicone copolyols, and alkyl dimethicone ethoxy glucosides.

29. The emulsion of claim 28, wherein the one or more water-in-oil emulsifiers comprise polyglyceryl-3 methylglucose distearate.

* * * * *